United States Patent [19]

Becker et al.

[11] Patent Number: 5,314,886
[45] Date of Patent: May 24, 1994

[54] N-SUBSTITUTED LACTAMS USEFUL AS CHOLECYSTOKININ ANTAGONISTS

[75] Inventors: Daniel P. Becker, Glenview; Daniel L. Flynn, Mundelein; Clara I. Villamil, Glenview, all of Ill.

[73] Assignee: G. D. Searle & Co., Chicago, Ill.

[21] Appl. No.: 968,617

[22] Filed: Oct. 29, 1992

Related U.S. Application Data

[62] Division of Ser. No. 626,590, Dec. 11, 1990, Pat. No. 5,202,344.

[51] Int. Cl.$^5$ .............. C07D 207/273; C07D 207/277; A61K 31/40
[52] U.S. Cl. .................................... 514/252; 514/314; 514/403; 514/414; 514/422; 514/423; 514/424; 544/406; 546/169; 548/362.5; 548/467; 548/517; 548/518; 548/531; 548/537; 548/550; 540/364
[58] Field of Search .................... 544/406; 546/169; 548/362.5, 467, 517, 518, 531, 537, 550; 514/252, 364, 403, 414, 422, 423, 424

[56] References Cited

U.S. PATENT DOCUMENTS

| | | | |
|---|---|---|---|
| 3,474,093 | 10/1969 | McCaully et al. | 260/247.1 |
| 4,200,572 | 4/1980 | Gleason et al. | 260/239 |
| 4,260,743 | 4/1981 | Bose | 542/442 |
| 4,757,068 | 7/1988 | Parsons | 514/213 |

FOREIGN PATENT DOCUMENTS 2748258  5/1978  Fed. Rep. of Germany ......... C07D 205/08

OTHER PUBLICATIONS

Bayer, et al. "Preparation and properties of mesoionic oxazolones," Chemical Abstract 73(15):77105c (1970).
J. A. Williams "Cholecystokinin: A Hormone and A Neurotransmitter," Biomedical Research 3(2), 107-121, (1982).
M. Albus "Cholecystokinin," Prog. Neuro-Psycholpharmacol & Biol. Psychiat. 1988, vol. 12, pp. S5-S21.
U. Scheurer "Mechanism of Action of Cholecystokinin Octapeptide on Rat Antrum, Pylorus and Duodenum," Am. J. Physiol. 244 G266-G272, (1983).
E. Corazziari "Oral Administration of Loxiglumide (CCK Antagonist) Inhibits Postprandial Gallbladder Contraction Without Affecting Gastric Emptying," Digestive Diseases and Sciences, 35(1), pp. 50-54, (Jan. 1990).

(List continued on next page.)

Assistant Examiner—Philip I. Datlow
Attorney, Agent, or Firm—Joy Ann Serauskas; Roger A. Williams

[57] ABSTRACT

This invention relates to novel N-substituted lactams having the following formula

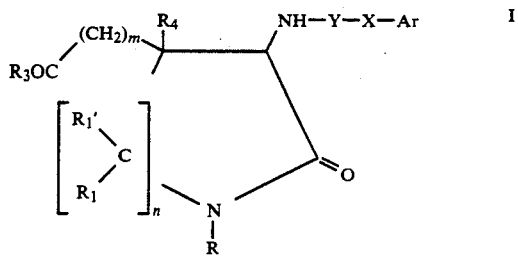

useful in the treatment and prevention of Cholecystokinin (CCK) related disorders of the gastrointestinal, central nervous and appetite regulatory systems of mammals.

29 Claims, No Drawings

OTHER PUBLICATIONS

R. Harvey "Effect of Cholecystokinin on Colonic Motility and Symptoms in Patients with Irritable-Bowel Syndrome," The Lancet, Saturday, Jan. 6, 1973, p. 7793.

C. Niederau "Caerulein-Induced Acute Necrotizing Pancreatitis in Mice: Protective Effects of Proglumide, Benzotript, and Secretin," Gastroenterology, 88, pp. 1192-1204 (1985).

P. L. Faris "Evidence for the Neuropeptide Cholecystokinin as an Antagonist of Opiate Analgesia," Science 219, pp. 310-312 (1983).

N. S. Baber "The Role of CCK, Caerulein, and CCK Antagonists in Nociception," Pain, 39, pp. 307-328, (1989).

G. P. Smith "Gut Hormone Hypothesis of Postprandial Satiety," Eating and Its Disorders, pp. 67-75 (1984).

S. Ravard "Cholecystokinin and Anxiety," Trends in Pharmacol. Sci., 11, pp. 271-273, (1990).

J. Crawley "Behavioral Analyses of Antagonists of the Peripheral and Central Effects of Cholecystokinin," Cholecystokinin Antagonists, pp. 243-262, (1988).

S. A. Watson "Effects of L-365,260, a Potent Gastrin Receptor Antagonist on the In Vitro Growth of Animal and Human Gastro-Intestinal Tumour Cells," Gut., 30, 1447, (1989).

B. Douglas "Modulation by CR-1409 (Loglumide), a Cholecystokinin Receptor Antagonist, of Trypsin Inhibitor-Enhanced Growth of Azaserine-Induced Putative Preneoplastic Lesions in Rat Pancreas," Cancer Research, 49, pp. 2438-2441, (1989).

D. S. Garvey "3 4-disubstituted gamma-lactam rings as conformationally constrained mimics of peptide derivatives containing aspartic acid or norleueine," Journal of Organic Chemistry, 55(3), pp. 936-940, (1990).

A. Malik "New Synthetic Routes to Amino Sugars and Sugar Amino Acids," Chemical Abstract, 112:7794b p. 767, (1990).

N-SUBSTITUTED LACTAMS USEFUL AS CHOLECYSTOKININ ANTAGONISTS

This is a division of application Ser. No. 07/626,590, filed Dec. 11, 1990 now U.S. Pat. No. 5,202,344.

FIELD OF THE INVENTION

The invention herein is directed to N-substituted lactams which can be useful in the treatment and prevention of cholecystokinin (CCK) related disorders of the gastrointestinal, central nervous and appetite regulatory systems of mammals by administering to a subject in need thereof a therapeutically effective amount of a compound disclosed herein or a pharmaceutically acceptable salt thereof. Therefore, the compounds of the invention find utility in GI motility disorders including irritable bowel syndrome, visceral pain, reversing satiety, and in treating anxiety. Also, the compounds of the invention are useful in the treatment of pancreatitis and pancreatic cancer.

BACKGROUND OF THE INVENTION

Cholecystokinin (CCK) is a brain/gut neuropeptide which has been implicated in a number of central nervous system and gastrointestinal disease states [Reviews: J. A. Williams, *Biomedical Research* (1982), 3, 107; M. Albus, *Prog. Neuro-Psychopharmacol & Biol. Psychiat.* (1988), 12, p S5]. Cholecystokinin in the GI tract evokes contraction of gut smooth musculature [U. Scheurer et al, *Am. J. Physiol.* (1983, 244. G266], and functionally causes delayed gastric emptying, contraction of the gall bladder [E. Corazziari et al, *Dig. Dis. & Sci.* (1990), 35, 50], initiation of the gastrocolic reflex [R. F. Harvey and A. E. Read, *The Lancet* (1973), Sat. 6 January, p. 7793]. CCK plays an important physiologic role in pancreatic function and secretion. Abnormalities of CCK have been implicated in causing pancreatitis [C. Niederau et al, *Gastroenterology* (1985), 88, 1192]. Abnormalities of CCK function in the GI tract may be causitive in a number of GI motility disorders, including irritable bowel syndrome. Additionally, CCK acts as a physiologic opiate antagonist, and has been reported to be hyperalgesic, and to inhibit analgesia produced by opiates [P. L. Faris et al, *Science* (1983), 219, 310; N. S. Baber et al, *Pain* (1989), 39. 307].

Actions of CCK in the Central nervous system have demonstrated a role for CCK in controling eating behavior (producing satiety) [G. P. Smith in *Eating and Its Disorders* (A. J. Stunkard & E. Stellar, Eds), (1984), pp. 67–75, Raven Press], in producing symptoms of panic disorder & other forms of anxiety [*Trends in Pharmacol. Sci.* (1990), 11, 271], and in modulating mesolimbic dopamine release [J. N. Crawley in *Cholecystokinin Antagonists* (R. Y. Wang R. Schoenfeld, eds., (1988), pp. 243–262, Alan R. Liss].

Finally, CCK and/or gastrin have been implicated as tumorgenic in a number of cancers, including cancers of the pancreas and the colon [S. A. Watson et al, *GUT* (1989, 30, 1447; B. R. Douglas et al, *Cancer Research* (1989), 49, 2438].

Thus, an antagonist to CCK at either the A-receptor subtype or the B-receptor subtype may be useful in the treatment of GI motility disorders (including irritable bowel syndrome), eating disorders where an anti-satiety effect is desired, panic-like anxiety, compulsive behavior and other CNS disorders.

U.S. Pat. No. 4,757,068 discloses a class of lactams and bicyclic lactams which are useful in the treatment and prevention of CCK-related disorders of the gastrointestinal, central nervous and appetite regulatory systems of mammals. The compounds of this disclosure are structurally distinct from the present invention. bicyclic β-lactam penicillin analogs having anti-bacterial activity. The compounds of this disclosure are distinct from the compounds of the present invention both in structure and utility.

U.S. Pat. No. 3,474,093 discloses pyrrolidinone, indolinone, cycloheptapyrrolone and cyclopentapyrrolone adducts of N-acyloxy-N-acylaminoacetanilides useful as hyperemic depressants, anti-convulsants and antiarrhythmic agents.

SUMMARY OF THE INVENTION

The present invention relates to a novel class of compounds represented by the formula

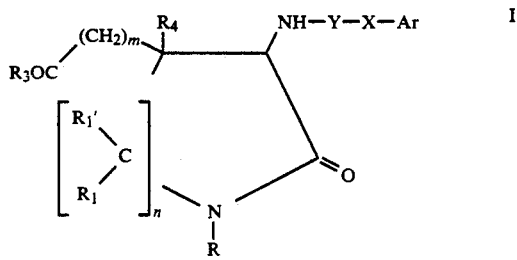

and isomers thereof; or a pharmaceutically acceptable acid or base addition salt thereof:

wherein

Ar is aryl; substituted aryl which can be substituted one or more by alkyl of 1 to 6 carbon atoms, alkoxy wherein the alkyl is 1 to 6 carbon atoms, trifluoromethyl, halogen, amino, alkyl or dialkyl substituted amino wherein the alkyl is 1 to 6 carbon atoms; heterounsaturated ring having 5 or 6 carbon atoms wherein one or two of the carbon atoms is replaced by nitrogen, oxygen or sulfur; substituted heterounsaturated ring having 5 or 6 carbon atoms wherein one or two of the carbon atoms is replaced by nitrogen, oxygen or sulfur which can be substituted once or more by alkyl of 1 to 6 carbon atoms, halogen or trifluoromethyl; fused bicyclic aromatic hydrocarbon radical having 9 or 10 carbon atoms; substituted fused bicyclic aromatic hydrocarbon radical having 9 or 10 carbon atoms which can be substituted one or more by alkyl of 1 to 6 carbon atoms, halogen, trifluoromethyl, amino, alkyl or dialkyl substituted amino wherein the alkyl is 1 to 6 carbon atoms or alkoxy wherein the alkyl is 1 to 6 carbon atoms; fused heterobicyclic hydrocarbon radical having 9 or 10 carbon atoms wherein one to three of the carbon atoms is replaced by nitrogen, oxygen or sulfur; substituted fused heterobicyclic hydrocarbon radical having 9 or 10 carbon atoms wherein one to three of the carbon atoms is replaced by nitrogen oxygen or sulfur which can be substituted one or more by alkyl of 1 to 6 carbon atoms, halogen, trifluoromethyl, amino, alkyl or dialkyl substituted amino wherein the alkyl is 1 to 6 carbon atoms or alkoxy wherein the alkyl is 1 to 6 carbon atoms.

R is alkyl having 1 to 8 carbon atoms wherein one of the carbon atoms may be replaced by oxygen; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy; aralkyl wherein the alkyl is 1 to 8 carbon atoms; substituted aralkyl wherein the alkyl is 1 to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy.

X is a direct bond or a substituent selected from the group consisting of NH, oxygen or alkylene having 1 to 3 carbon atoms.

n is an integer from 0 to 1.

$R_1$ and $R'_1$ are each independently hydrogen or alkyl having 1 to 4 carbon atoms.

m is an integer from 0 to 3

$R_3$ is OH, $OR_5$ wherein $R_5$ is alkyl having 1 to 6 carbon atoms, $NR_6R_7$ wherein $R_6$ and $R_7$ are each independently hydrogen or alkyl of 1 to 6 carbon atoms or $NR_8R_9$ which together form a five to seven membered ring wherein $R_8$ and $R_9$ represent an alkylene group having four to six carbon atoms and one of the alkylenes may be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms.

$R_4$ is hydrogen or alkyl having 1 to 4 carbon atoms.

Y is C=O or $SO_2$.

The invention further relates to pharmaceutical compositions comprising a compound of formula I. Such compounds and compositions can be useful in the treatment and prevention of cholecystokinin (CCK) related disorders of the gastrointestinal, central nervous and appetite regulatory systems.

A preferred embodiment of the present invention are compounds of the formula

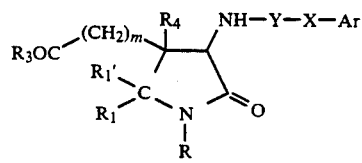

II and isomers thereof; or a pharmaceutically acceptable acid or base addition salt thereof:

wherein

Ar is aryl; substituted aryl which can be substituted one or more by alkyl of 1 to 6 carbon atoms, alkoxy wherein the alkyl is 1 to 6 carbon atoms, trifluoromethyl, halogen, amino, alkyl or dialkyl substituted amino wherein the alkyl is 1 to 6 carbon atoms; heterounsaturated ring having 5 or 6 carbon atoms wherein one or two of the carbon atoms is replaced by nitrogen, oxygen or sulfur; substituted heterounsaturated ring having 5 or 6 carbon atoms wherein one or two of the carbon atoms is replaced by nitrogen, oxygen or sulfur which can be substituted once or more by alkyl of 1 to 6 carbon atoms, halogen or trifluoromethyl; fused bicyclic aromatic hydrocarbon radical having 9 or 10 carbon atoms; substituted fused bicyclic aromatic hydrocarbon radical having 9 or 10 carbon atoms which can be substituted one or more by alkyl of 1 to 6 carbon atoms, halogen, trifluoromethyl, amino, alkyl or dialkyl substituted amino wherein the alkyl is 1 to 6 carbon atoms or alkoxy wherein the alkyl is 1 to 6 carbon atoms; fused heterobicyclic hydrocarbon radical having 9 or 10 carbon atoms wherein one to three of the carbon atoms is replaced by nitrogen, oxygen or sulfur; substituted fused heterobicyclic hydrocarbon radical having 9 or 10 carbon atoms wherein one to three of the carbon atoms is replaced by nitrogen oxygen or sulfur which can be substituted one or more by alkyl of 1 to 6 carbon atoms, halogen, trifluoromethyl, amino, alkyl or dialkyl substituted amino wherein the alkyl is 1 to 6 carbon atoms or alkoxy wherein the alkyl is 1 to 6 carbon atoms.

R is alkyl having 1 to 8 carbon atoms wherein one of the carbon atoms may be replaced by oxygen; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy; aralkyl wherein the alkyl is 1 to 8 carbon atoms; substituted aralkyl wherein the alkyl is 1 to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl or methylene dioxy.

X is a direct bond or a substituent selected from the group consisting of NH, oxygen or alkylene having 1 to 3 carbon atoms.

$R_1$ and $R_1'$ are each independently hydrogen or alkyl having 1 to 4 carbon atoms.

m is an integer from 0 to 3

$R_3$ is OH, $OR_5$ wherein $R_5$ is alkyl having 1 to 6 carbon atoms, $NR_6R_7$ wherein $R_6$ and $R_7$ are each independently hydrogen or alkyl of 1 to 6 carbon atoms or $NR_8R_9$ which together form a five to seven membered ring wherein $R_8$ and $R_9$ represent an alkylene group having four to six carbon atoms and one of the alkylenes may be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms.

$R_4$ is hydrogen or alkyl having 1 to 4 carbon atoms.

Y is C=O or $SO_2$.

A further preferred embodiment of the present invention are compounds of the formula

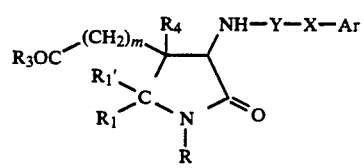

II and isomers thereof; or a pharmaceutically acceptable acid or base addition salt thereof:

wherein

Ar is aryl; substituted aryl which can be substituted one or more by alkyl of 1 to 6 carbon atoms, alkoxy wherein the alkyl is 1 to 6 carbon atoms, trifluoromethyl, halogen, amino, or alkyl or dialkyl substituted amino wherein the alkyl is 1 to 6 carbon atoms; heterounsaturated ring having 5 or 6 carbon atoms wherein one or two of the carbon atoms is replaced by nitrogen, oxygen or sulfur; substituted heterounsaturated ring having 5 or 6 carbon atoms wherein one or two of the carbon atoms is replaced by nitrogen, oxygen or sulfur which can be substituted once or more by alkyl of 1 to 6 carbon atoms, halogen or trifluoromethyl;

R is alkyl having 1 to 8 carbon atoms; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl or methylene dioxy or; aralkyl wherein the alkyl is 1 to 8 carbon atoms.

$R_1$ and $R_1'$ are each independently hydrogen or alkyl having 1 to 4 carbon atoms.

m is an integer from 0 to 3

$R_3$ is OH or $OR_5$ wherein $R_5$ is alkyl having 1 to 6 carbon atoms.

$R_4$ is hydrogen

X is a direct bond or a substituent selected from the group consisting of NH, oxygen or alkylene having 1 to 3 carbon atoms.

Y is C=O or $SO_2$.

Exemplifying this embodiment are the following compounds.

cis-4-[[(3,4-dichlorophenyl)carbonyl]amino]-5-oxo-1-pentyl-3-pyrrolidinecarboxylic acid.
trans-4-[[(4-chlorophenyl)carbonyl]amino]-5-oxo-1-pentyl-3-pyrrolidinecarboxylic acid.
trans-4-[[[(4-chlorophenyl)amino]carbonyl]amino]-5-oxo-1-pentyl-3-pyrrolidinecarboxylic acid.
cis-4-[[[(4-chlorophenyl)amino]carbonyl]amino]-5-oxo-1-pentyl-3-pyrrolidinecarboxylic acid.
cis-4-[[[(3,4-dichlorophenyl)amino]carbonyl]amino]-5-oxo-1-pentyl-3-pyrrolidinecarboxylic acid.
cis-4-[[(4-chlorophenyl)carbonyl]amino]-5-oxo-1-phenyl-3-pyrrolidinecarboxylic acid.
trans-4-[[(4-chlorophenyl)carbonyl]amino]-5-oxo-1-phenyl-3-pyrrolidinecarboxylic acid.
cis-4-[[(3,4-dichlorophenyl)carbonyl]amino]-5-oxo-1-phenyl-3-pyrrolidinecarboxylic acid.
trans-4-[[(3,4-dichlorophenyl)carbonyl]amino]-5-oxo-1-phenyl-3-pyrrolidinecarboxylic acid.
trans-4-[[[(3,4-dichlorophenyl)amino]carbonyl]amino-5-oxo-1-phenyl-3-pyrrolidinecarboxylic acid.
cis-4-[[[3,4-dichlorophenyl)amino]carbonyl]amino]-5-oxo-1-phenyl-3-pyrrolidinecarboxylic acid.
cis-4-[[(3,4-dichlorophenyl)sulfonyl]amino]-5-oxo-1-phenyl-3-pyrrolidinecarboxylic acid.
cis-5-oxo-1-phenyl-4-[(2-pyrazinylcarbonyl)amino]-3-pyrrolidinecarboxylic acid
cis-4-[[(3,4-dichlorophenyl)carbonyl]amino]-5-oxo-1-(phenylmethyl)-3-pyrrolidinecarboxylic acid
cis-4-[[[(3,4-dichlorophenyl)amino]carbonyl]amino]-5-oxo-1-(methylphenyl)-3-pyrrolidinecarboxylic acid
trans-4-[[[(4-chlorophenyl)amino]carbonyl]amino]-5-oxo-1-phenyl-3-pyrrolidinecarboxylic acid Another preferred embodiment of the present invention are compounds of the formula

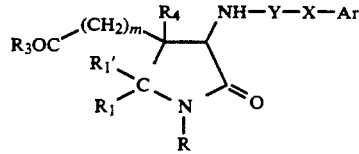

and isomers thereof; or a pharmaceutically acceptable acid or base addition salt thereof:

wherein

Ar is fused bicyclic aromatic hydrocarbon radical having 9 or 10 carbon atoms; substituted fused bicyclic aromatic hydrocarbon radical having 9 to 10 carbon atoms which can be substituted one or more by alkyl of 1 to 6 carbon atoms, halogen, trifluoromethyl amino, alkyl or dialkyl substituted amino wherein the alkyl is 1 to 6 carbon atoms, or alkoxy wherein the alkyl is 1 to 6 carbon atoms.

R is alkyl having 1 to 8 carbon atoms; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy; aralkyl wherein the alkyl is 1 to 8 carbon atoms; substituted aralkyl wherein the alkyl is ; to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy;

$R_1$ and $R_1'$ are each independently hydrogen or alkyl having 1 to 4 carbon atoms.

m is an integer from 0 to 3

$R_3$ is OH, $OR_5$ wherein $R_5$ is alkyl having 1 to 6 carbon atoms, $NR_6R_7$ wherein $R_6$ and $R_7$ are each independently hydrogen or alkyl of 1 to 6 carbon atoms or $NR_8R_9$ which together form a five to seven membered ring wherein $R_8$ and $R_9$ represent an alkylene group having four to six carbon atoms and one of the alkylenes may be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms.

$R_4$ is hydrogen

Y is C=O or $SO_2$

X is a driect bond or a substituent selected from the group consisting of NH, oxygen or alkylene having 1 to 3 carbon atoms.

Exemplifying this embodiment are the following compounds:

trans-4-[(2-naphthalenylcarbonyl]amino-5-oxo-1-pentyl-3-pyrrolidinecarboxylic acid.
cis-1-[(2-fluorophenyl)-4-[(2-naphthalenylcarbonyl)amino]-5-oxo-3-pyrrolidinecarboxylic acid.
cis-4-[[(2-naphthalenylamino)carbonyl]amino]-5-oxo-1-pentyl-3-pyrrolidinecarboxylic acid.
cis-4-[(2-naphthalenylcarbonyl)amino]-5-oxo-1-phenyl-3-pyrrolidinecarboxylic acid.
trans-4-[(2-naphthalenylcarbonyl)amino]-5-oxo-1-phenyl-3-pyrrolidinecarboxylic acid.
cis-1-[[3-[(2-naphthalenylcarbonyl)amino]-2-oxo-1-phenyl-4-pyrrolidinyl]carbonyl]pyrrolidine
trans-1-[[3-[(2-naphthalenylcarbonyl)amino]-2-oxo-1-phenyl-4-pyrrolidinyl]carbonyl]pyrrolidine
trans-4-[[(2-naphthalenylamino)carbonyl]amino]-5-oxo-1-phenyl-3-pyrrolidinecarboxylic acid
1,1-dimethylethyl cis-4-[(2-naphthalenylcarbonyl)amino]-5-oxo-1-phenyl-3-pyrrolidinecarboxylate
cis-4-[(2-naphthalenylcarbonyl)amino]-5-oxo-1-(phenylmethyl)-3-pyrrolidinecarboxylic acid
cis-4-[(2-naphthalenylsulfonyl)amino]-5-oxo-1-phenyl-3-pyrrolidinecarboxylic acid Another further preferred embodiment of the present invention are compounds of the formula

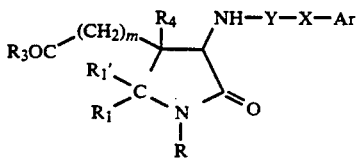

and isomers thereof; or a pharmaceutically acceptable acid or bas addition salt thereof:
wherein
Ar is fused heterobicyclic hydrocarbon radical having 9 or 10 carbon atoms wherein one to three of the carbon atoms is replaced by nitrogen, oxygen or sulfur; substituted fused heterobicyclic hydrocarbon radical having 9 or 10 carbon atoms wherein one to three of the carbon atoms is replaced by nitrogen oxygen or sulfur which can be substituted one or more by alkyl of 1 to 6 carbon atoms, halogen, trifluoromethyl, amino, alkyl or dialkyl substituted amino wherein the alkyl is 1 to 6 carbon atoms, or alkoxy wherein the alkyl is 1 to 6 carbon atoms.
R is alkyl having 1 to 8 carbon atoms; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy; aralkyl wherein the alkyl is 1 to 8 carbon atoms; substituted aralkyl wherein the alkyl is 1 to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy.
$R_1$ and $R_1'$ are each independently hydrogen or alkyl having 1 to 4 carbon atoms.
m is an integer from 0 to 3
$R_3$ is OH, $OR_5$ wherein $R_5$ is alkyl having 1 to 6 carbon atoms, $NR_6R_7$ wherein $R_6$ and $R_7$ are each independently hydrogen or alkyl of 1 to 6 carbon atoms or $NR_8R_9$ which together form a five to seven membered ring wherein $R_8$ and $R_9$ represent an alkylene group having four to six carbon atoms and one of the alkylenes may be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms.
$R_4$ is hydrogen
Y is C=O
X is a direct bond or a substituent selected from the group consisting of NH, oxygen or alkylene having 1 to 3 carbon atoms.
Exemplifying this embodiment are the following compounds:
trans-N-[2-oxo-1-phenyl-4-(1-pyrrolidinylcarbonyl)-3-pyrrolidinyl]-1H-indole-2-carboxamide
cis-4-[(1H-indol-2-ylcarbonyl)amino]-5-oxo-1-[phenylmethyl]-3-pyrrolidinecarboxylic acid
cis-4-[(1H-indazol-3-ylcarbonyl)amino]-5-oxo-1-phenyl-3-pyrrolidinecarboxylic acid
cis-4-[(1H-indol-2-ylcarbonyl)amino]-5-oxo-1-phenyl-3-pyrrolidinecarboxylic acid.
cis-1-(2-fluorophenyl)-5-oxo-4-[(3-quinolinylcarbonyl)amino]-5-oxo-3-pyrrolidinecarboxylic acid.
trans-4-[(1-H-indol-3-acetyl)amino]-5-oxo-1-phenyl-3-pyrrolidinecarboxylic acid.
cis-5-oxo-1-pentyl-4-[(3-quinolinylcarbonyl)amino]-3-pyrrolidinecarboxylic acid, monohydrochloride.
trans-4-[(1H-indol-2-ylcarbonyl)amino]-5-oxo-1-phenyl-3-pyrrolidinecarboxylic acid.

As used herein, the term "alkyl of 1 to 8 carbon atoms" refers to straight chain or branched chain hydrocarbon groups having from 1 to 8 carbon atoms. Illustrative of such alkyl groups are methyl, ethyl, propyl, isopropyl, butyl, isobutyl pentyl, neopentyl, hexyl, isohexyl and octyl.

As used herein, the term "alkoxy wherein the alkyl is 1 to 6 carbon atoms" refers to straight or branched chain ethers. Illustrative of such groups are methoxy, ethoxy, propoxy, butoxy and isopropoxy.

As used herein, the term "amino" refers to the group—$NH_2$; "alkyl or dialkyl substituted amino wherein the alkyl is 1 to 6 carbon atoms" refers to the replacement of hydrogen by an alkyl group.

As used herein, the term "alkylene having 1 to 3 carbon atoms" refers to straight or branched saturated hydrocarbon groups having from one to three carbon atoms. Illustrative of such groups are methylene, ethylene, trimethylene, and methylethylene.

The term "aryl" represents phenyl or biphenyl.

As used herein, the term "halogen" includes fluoro, chloro and bromo.

As used herein, the term "$NR_8R_9$ which together form a five to seven membered ring wherein $R_8$ and $R_9$ together represent an alkylene group having four to six carbon atoms and one of the carbon atoms may be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms" refers to heterosaturated cyclic radical having 5 to 7 atoms wherein one of the atoms is nitrogen and the remaining atoms are carbon atoms wherein one of the carbon atoms may be optionally replaced by oxygen, nitrogen or $NR_{10}$ wherein $R_{10}$ is defined as above. Illustrative of such radicals are morpholinyl, pyrazolinyl, piperazinyl and 4-methyl piperizin-1-yl.

As used herein, the term "heterounsaturated ring having 5 or 6 carbon atoms wherein one or two of the carbon atoms is replaced by nitrogen, sulfur or oxygen" refers to a heterounsaturated cyclic radical having 5 or 6 carbon atoms wherein one or two of the carbons is replaced by nitrogen, sulfur or oxygen. Illustrative of such radicals are pyrrolyl, imidazolyl, pyrazolyl, pyridinyl, pyrazinyl, pyrimidinyl, pyranyl, furanyl, thiophenyl, isothiazolyl, isoxazolyl, pyrazolinyl, and imidazolinyl, oxazolyl, and thiazolyl.

As used herein, the term "fused bicyclic aromatic hydrocarbon radical having 9 or 10 carbon atoms" refers to aromatic hydrocarbons composed of two fused rings having a maximum number of 10 carbons. Illustrative of such radicals are naphthalenyl and indenyl.

As used herein, the term "fused heterobicyclic hydrocarbon radical having 9 or 10 carbon atoms wherein one to three of the carbon atoms is replaced by nitrogen, oxygen or sulfur" refers to hydrocarbons composed of two fused rings having a maximum of 10 carbons wherein one to three of the carbon atoms is replaced by nitrogen, oxygen or sulfur. Illustrative of such radicals are indolizinyl, isoindolyl, indolyl, indazolyl, benzofuranyl, isobenzofuranyl, chromenyl, benzothiophenyl, quinolizinyl, isoquinolinyl, quinolinyl, imidazopyridinyl, pyridinopyridinyl, phthalazinyl, naphthyridinyl, indolinyl, and chromanyl.

Included within the embodiments of the present invention are the tautomeric forms of the described compounds, isomeric forms including geometric isomers, enantiomers and diastereoisomers, and the pharmaceutically acceptable salts thereof.

The term "pharmaceutically-acceptable salts" embraces salts commonly used to form alkali metal salts and to form addition salts of free acids or free bases. Since the compounds of Formulas I, II and III contain basic nitrogen atoms, such salts are typically acid addition salts or quaternary salts. The nature of the salt is not critical, provided that it is pharmaceutically acceptable, and acids which may be employed to form such salts are, of course, well known to those skilled in this art. Examples of acids which may be employed to form pharmaceutically acceptably acid addition salts include such inorganic acids as hydrochloric acid, sulphuric acid and phosphoric acid, and such organic acids as maleic acid, succinic acid and citric acid. Other pharmaceutically acceptably salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I, II and III.

SCHEME I:
SYNTHESIS OF PYRRIDINONE CCK ANTAGONISTS

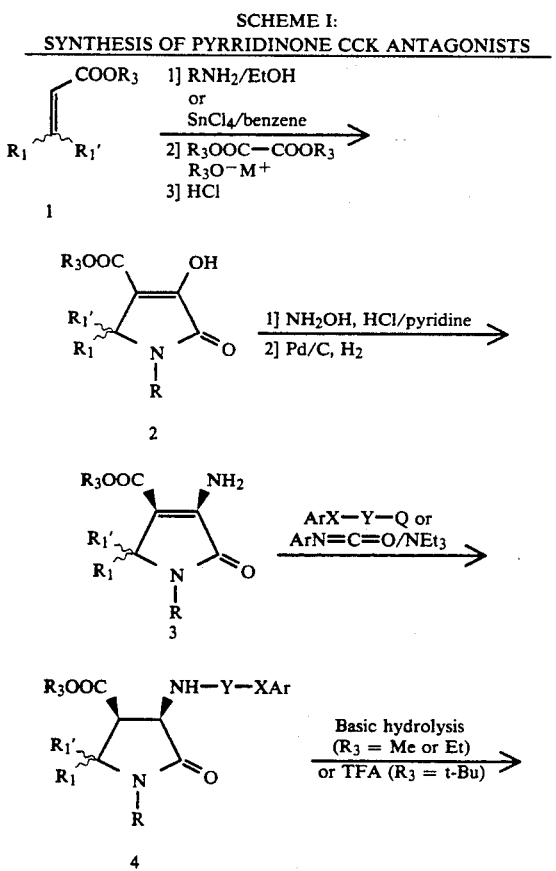

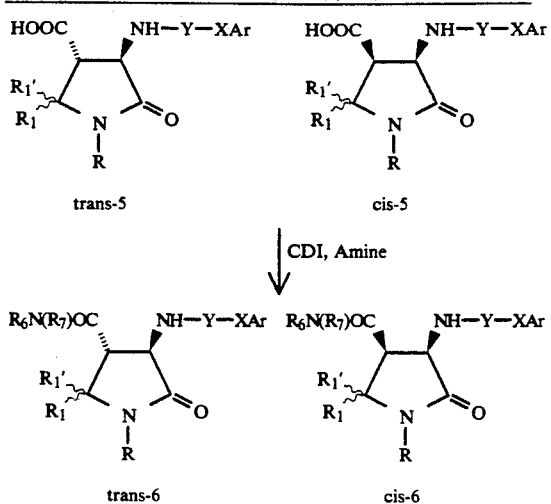

The synthesis of compounds of Formula I wherein n equals 1 and R, $R_1$, $R'_1$, Ar, m, Y and X are defined as before and $R_4$ is hydrogen, $R_3$ is OH or $OR_5$ wherein $R_5$ is alkyl of 1 to 6 carbon atoms and (Scheme I) involves the use of methodology reported by Southwick et al. [*J. Org. Chem.* 21, 1087 (1956) & *J. Am. Chem. Soc.* 75, 3413 (1953)] for the preparation of intermediate 2. Thus the appropriate acrylate ester 1 optionally mono- or di-substituted in the beta position is reacted with the desired aliphatic or aromatic amine ($RNH_2$). For an aliphatic amine, the reaction is carried out in ethanol; whereas, for an aromatic amine, the reaction is accomplished in benzene with an acid catalyst such as tin tetrachloride. Subsequent reaction of the intermediate beta-amino ester species with the appropriate oxalate diester and the corresponding alkoxide followed by quenching with an acid, preferably HCl, gives the pyrrolidinone 2. The oximes 2' are formed by reaction of 2 with hydroxylamine hydrochloride in pyridine. Hydrogenation of the resulting oxime with palladium on carbon proceeds stereospecifically to give the cis-substituted aminopyrrolidinone 3. N-acylation of 3 with (hetero)arylacids by using one of several common acid-activating reagents [CDI, DCC, $SOCl_2$] gives the amide 4 [X is direct bond or $CH_2$]. Alternatively, treating 3 with an appropriate isocyanate or haloformate in the presence of a base such as triethylamine affords the pyrrolidinone urea [X=NH] or urethane [X=O] 4 respectively. Saponification of the ester moiety of 4 (for $R_3$=Me, Et) affords the trans-substituted pyrrolidinone carboxylic acid 5. Alternatively ester cleavage of 4 (for $R_3$=tert butyl) may be accomplished with an acid, preferably trifluoroacetic acid, affording the cis-substituted pyrrolidinone carboxylic acid 5.

The amides trans-6 and cis-6 are prepared by coupling trans-5 or cis-5, respectively, with an appropriate amine utilizing an acid-activating agent such as carbonyldiimidazole (CDI).

SCHEME II: SYNTHESIS OF HOMOLOGATED PYRROLIDINONES

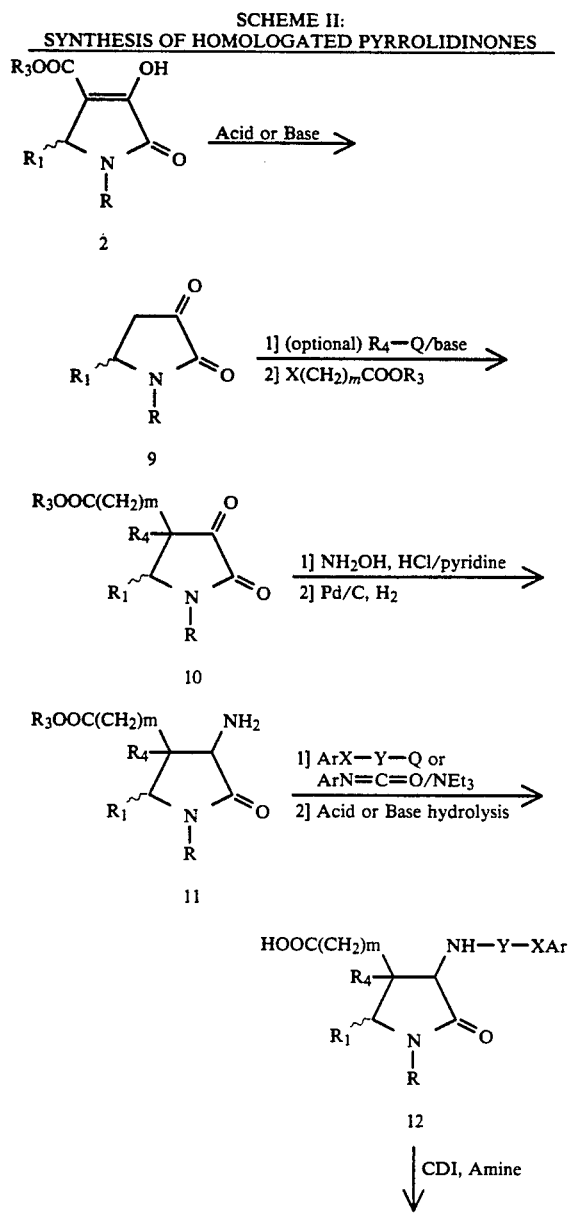

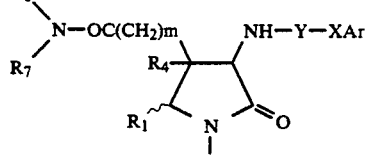

The synthesis of homologated pyrrolidinones (m=1 to 3) of Formula I wherein $R_4$ is hydrogen or alkyl (Scheme II) again relies on methodology reported by Southwick (vide supra) for the preparation of intermediates 9. Hydrolysis and decarboxylation of pyrrolidinone ester 2 proceeds under acidic or basic conditions to give ketopyrrolidinone 9. The ketone 9 may optionally be alkylated in the 4-position (R4) by treatment with a base such as LDA and quenching with an alkylating agent R-Q such as methyl iodide. Subsequent reaction under basic conditions with an alkylating agent such as ethyl bromoacetate yields the alkylated ketopyrrolidinone 10. Formation of the oxime of ketone 10 with hydroxylamine hydrochloride in pyridine followed by hydrogenation with palladium on carbon affords the aminopyrrolidinone 11. N-acylation of 11 with (hetero)arylacids using above-described acid-activating reagents followed by ester hydrolysis affords the pyrrolidinone amide 12 [X is direct bond or $CH_2$]. Alternatively, treating 11 with an appropriate isocyanate or an appropriate haloformate in the presence of a base such as triethylamine followed by ester hydrolysis affords the urea 12 [X=NH] or urethane 12 [X=O], respectively. The amides 13 are prepared by coupling 12 with the appropriate amine utilizing an acid-activating agent such as carbonyldiimidazole (CDI).

SCHEME III: CHIRAL SYNTHESIS OF PYRROLIDINONES
[* and ** indicate individual isomers]

-continued
SCHEME III: CHIRAL SYNTHESIS OF PYRROLIDINONES
[* and ** indicate individual isomers]

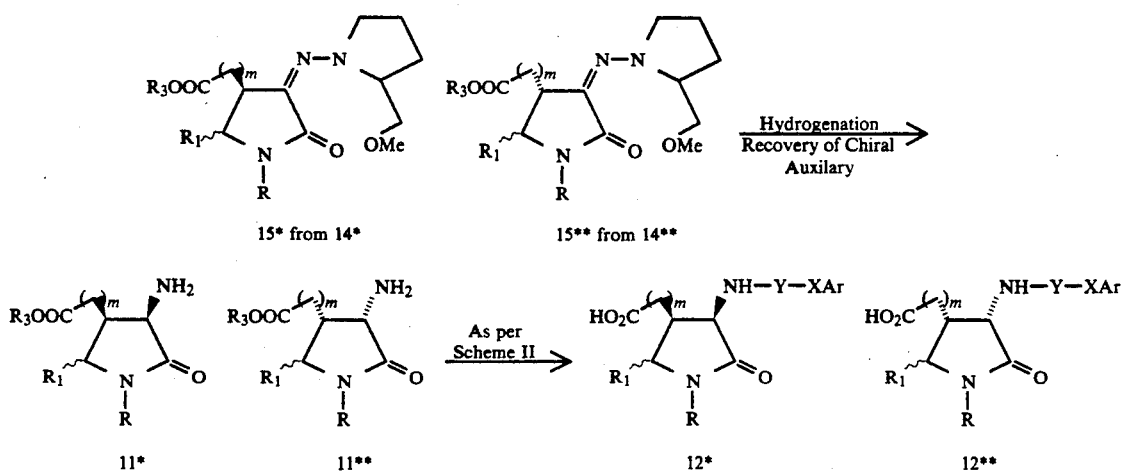

The synthesis of nonracemic pyrrolidinones of (Scheme III) utilizes methodology described by Dieter Enders et al. (*Org. Syn.* 65, 183 (1987)] to form the nonracemic intermediates 11* and 11**. Thus, reaction of ketopyrrolidinone 9 with commercially-available hydrazines (S)- or (R)-1-amino-2-methoxymethylpyrrolidine (SAMP or RAMP, respectively) in benzene under Dean-Stark conditions affords the corresponding hydrazone 14* or 14**. Reaction of each hydrazone individually under basic conditions with an electrophile such as ethyl bromoacetate affords alkylated hydrazones 15* and 15** in high diastereomeric excess. Removal of the hydrazone under hydrogenolysis conditions affords the cis-substituted aminopyrrolidinone 11* or 11**, depending upon the particular chiral hydrazine used. Coupling of the amines 11* and 11** followed by ester saponification proceeds as in Scheme II to afford the nonracemic cis-substituted pyrrolidinone 12* and 12** amides [X is a direct bond or $CH_2$], ureas [X=NH], and urethanes [X=O] as described above in Scheme II.

SCHEME IV: SYNTHESIS OF BETA-LACTAM CCK ANTAGONISTS

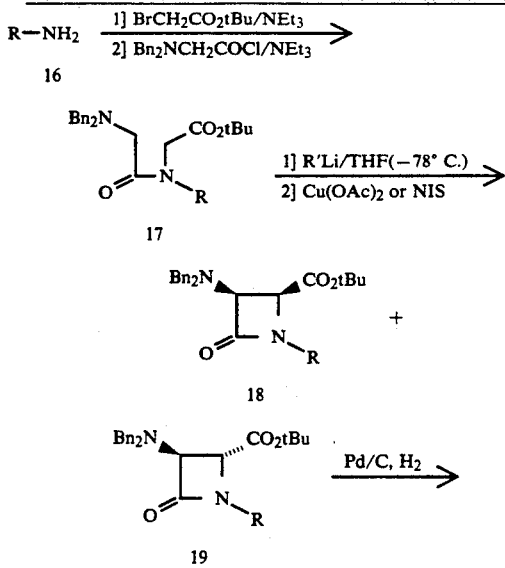

-continued
SCHEME IV: SYNTHESIS OF BETA-LACTAM CCK ANTAGONISTS

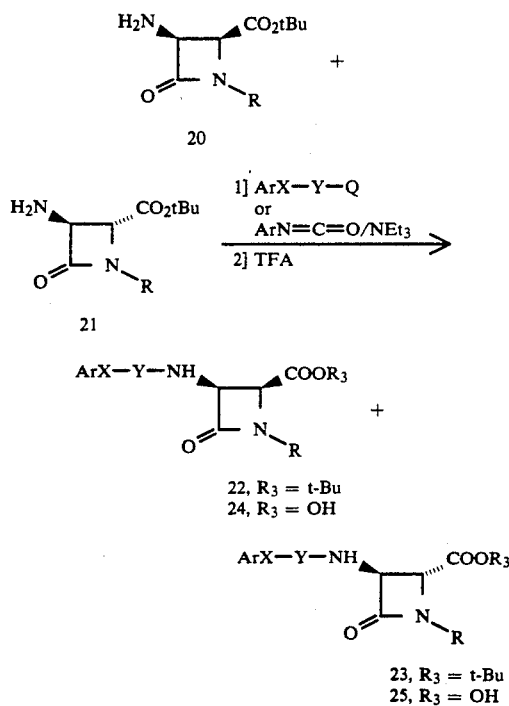

The synthesis of β-lactam of Formula I wherein n=o (Scheme IV) involves the use of methodology reported by T. Kawabata et al. [*J. Amer. Chem. Soc.* (1989), 111, 6843 & Tetrahedron Letters (1989), 30, 4837] for the preparation of intermediates 20 and 21. Thus, the appropriate aliphatic or aromatic amine 16 is reacted sequentially with t-butylbromoacetate/triethylamine and N,N-dibenzylglycine acid chloride/triethylamine to afford the intermediates of general structure 17. Dianion formation with two equivalents of alkyllithium base, followed by treatment with $Cu(OAc)_2$ gives predominantly the trans-substituted azetidinone 19. Alternatively, substituting the reagent N-iodosuccinimide (NIS) in the second step affords predominately the cis-substituted azetidinone 18. When the amine 16 contains a homochiral R group, the azetidinones 18 & 19 may be prepared asymmetrically.

Deprotection of the dibenzylamine moiety by hydrogenolysis gives the 3-aminoazetidinones 20 and 21 from 18 and 19, respectively. N-Acylation with (hetero)arylacids by using one of several common acid-activating reagents [CDI, DCC, $SOCl_2$] affords the corresponding amides 22a or 23a [X is direct bond or $CH_2$]. Alternatively, treating 20 or 21 with an appropriate isocyanate affords ureas 22b or 23b [X=NH]. Alternatively, treating 20 or 21 with the appropriate haloformate gives rise to urethanes 22c or 23c [X=O]. Alternatively, treating 20 or 21 with an (hetero)aryl sulfonylchloride in the presence of base such as triethylamine gives sulfonamides of formulae 22 or 23 (Y=$SO_2$). Compounds of general formulae 22 and 23 are converted to the carboxylic acids 24 and 25 by treatment with an acid, preferably trifluoroacetic acid.

This invention also relates to a method of treatment and prevention of cholecystokinin (CCK) related disorders of the gastrointestinal, central nervous and appetite regulatory systems of mammals, and more specifically, a method of treatment involving the administration of compounds of Formula I as the active ingredient.

For the treatment and prevention of CCK related disorders compounds of Formula I may be administered orally, topically, parenterally, or by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients. The compounds and composition may for example be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 1 to 250 mg preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight.

The dosage regimen for treating an infectious disease condition with the compounds and/or compositions of this invention is selected in accordance with a variety of factors, including the type, age, weight, sex and medical condition of the patient; the severity of the infection; the route of administration; and the particular compound employed and thus may vary widely.

For therapeutic purposes, the compounds of this invention are ordinarily combined with one or more adjuvants appropriate to the indicated route of administration. If per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include for example, water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

Dosage levels of the order from about 0.01 mg to about 10 mg per kilogram of body weight per day are useful in the treatment of the above-indicated conditions (from about 10 mg to about 1000 mg per patient per day).

The amount of active ingredient that may be combined with the carrier materials to produce a single dosage form will vary depending upon the host treated and the particular mode of administration. For example, a formulation intended for the oral administration of subjects may contain from 5 mg to 1.0 g of active agent compounded with an appropriate and convenient amount of carrier material which may vary from about 5 to 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to further illustrate the present invention and not to limit the invention in spirit or scope. In the Examples, all parts are parts by weight unless otherwise expressly set forth.

Preparation of Starting Materials

EXAMPLE A

Preparation of Ethyl 3-(phenylamino)propanoate

According to the procedure of P. L. Southwick, J. Am. Chem. Soc. 75 3413 (1953), to a solution of aniline (31.86 g, 0.35 mol) and ethyl acrylate (35.0 g, 0.35 mol) in 200 ml of dry benzene (freshly distilled from $CaH_2$) was added 0.5 ml of tin tetrachloride and the resulting solution was heated under reflux for 24 h. After cooling to room temperature the suspension was filtered to remove the inorganic solids and then concentrated in vacuo to give a dark green oil which was chromatographed on silica gel eluting with ethyl acetate/toluene (30/70) to give the title compound (40.7 g, 60%) as a light yellow oil. B.p. 95°–98° C. at 0.1 mm Hg.

EXAMPLE B

Preparation of 1,1-Dimethylethyl 3-(phenylamino)propanoate

To a solution of aniline (27.9 g, 0.30 mol) and tert-butyl acrylate (38.4 g, 0.30 mol) in dry benzene (500 ml) was added tin tetrachloride (2 ml) and the resulting solution was heated under reflux for 18 h. The resulting suspension was filtered and the filtrate was concentrated in vacuo giving a residue which was chromatographed on silica gel eluting with 25/75 ethyl acetate/hexane to give the title compound (22.53 g, 34%) as an oil. $^1$H NMR (300 MHz, $CDCl_3$) δ7.12 (2H, t), 6.71 (1H, m), 6.62 (2H, d), 3.40 (2H, t), 2.54 (2H, t), 1.44 (9H, s).

EXAMPLE C

Preparation of 1,1-Dimethylethyl 3-[(2-fluorophenyl)amino]propanoate

To a solution of 2-fluoroaniline (22.06 g, 0.198 mol) and freshly distilled tert-butyl acrylate (25.45 g, 0.198 mol) in dry benzene (250 ml) was added tin tetrachloride (1 ml) and the mixture was refluxed for 60 h. The resulting suspension was filtered and the filtrate was evaporated to give a semisolid which was chromatographed on silica gel eluting with 25/75 ethyl acetate/hexane to give the title compound (5.4 g, 11%). Anal calcd for $C_{13}H_{18}NO_2F$: C, 65.25; H, 7.58; N, 5.85. Found: C, 65.49; H, 7.75; N, 5.80.

MS M+1 calcd for $C_{13}H_{18}NO_2F$ 240, found 240.

EXAMPLE D

Preparation of Ethyl 2,5-dihydro-4-hydroxy-5-oxo-1-pentyl-1H-pyrrole-3-carboxylate The title compound was prepared by the general method of Southwick [J. Org. Chem. 21, 1087 (1956)]. Thus to a solution of n-pentylamine (8.04 g, 92.3 mmol) in 50 ml of dry EtOH was added ethyl acrylate (9.24 g, 92.3 mmol) with stirring under nitrogen at room temperature. After 18 h at room temperature, diethyl oxalate (13.5 g, 92.3 mmol) was added followed by a solution of sodium ethoxide in EtOH [made from sodium (2.12 g, 92.3 mmol) in 50 ml of dry EtOH]. The reaction mixture was then heated under reflux for 1 hour. To the resulting suspension was added 150 ml $H_2O$ and the reaction mixture was then concentrated under a stream of nitrogen to remove the EtOH. The white solid was then dissolved in 200 ml $H_2O$ and the solution was acidified with concentrated aqueous HCl (8.9 ml of a 10.4N solution). The resulting crystals were filtered, washed with water and dried to give the title compound (15.9 g, 71.4%) as colorless plates: mp 122°–123° C. Anal calcd for $C_{12}H_{19}NO_4$: C, 59.74; H, 7.94; N, 5.80. Found: C, 59.46; H, 7.87; N, 5.83.

EXAMPLE E

Preparation of Ethyl 2,5-dihydro-4-hydroxy-5-oxo-1-phenyl-1H-pyrrole-3-carboxylate The title compound was prepared as described by Southwick in J. Am. Chem. Soc. 75 3413 (1953). Thus to a solution of ethyl 2-phenylaminopropionate (40.7 g, 0.211 mol) and diethyl oxalate (30.8 g, 0.211 mol) in EtOH (250 ml, freshly distilled from Na) cooled to −3° C. was added via cannula a solution of sodium ethoxide in EtOH freshly made from 280 ml EtOH and sodium (4.85 g, 0.211 mol). The temperature was maintained below 5° C. throughout the addition. After the addition was complete the solution was allowed to warm to room temperature and stirring was continued overnight. The resulting slurry was acidified with 15% HCl to pH=2 and the resulting precipitate was filtered to give the title compound (29.3 g, 56%) as a colorless powder. Calcd for $C_{13}H_{13}NO_4$: C, 63.15; H, 5.30; N, 5.66. Found C, 62.68; H, 5.31; N, 5.55. DSC=155.98°–158.33° C. at 130.5 J/g.

EXAMPLE F

Preparation of 1,1-Dimethylethyl 2,5-dihydro-4-hydroxy-5-oxo-1-pentyl-1H-pyrrole-3-carboxylate To a solution of n-pentyl amine (21.72 g, 0.25 mol) in 110 ml of EtOH (freshly distilled from sodium) was added tert-butyl acrylate (36.62 ml, 0.26 mol) via syringe and the resulting solution was stirred under an atmosphere of argon for 12 h at room temperature. To the solution was then added diethyl oxalate (36.54 g, 0.25 mol). The solution was then cooled to 0° C. and a freshly prepared solution of sodium ethoxide (from 5.75 g (.25 mole) of sodium and 75 ml of EtOH) was added via cannula while maintaining the temperature between 0° C. and 5° C. After the addition was complete, the solution was allowed to warm to room temperature and stirred overnight. To the resulting slurry was added 400 ml of water followed the slow addition of 30% aqueous HCl to acidify to pH=4. The suspension was then extracted with $CH_2Cl_2$. The organic phase was dried over $MgSO_4$, filtered, and concentrated in vacuo to give a white solid. Recrystallization from ethyl acetate gave the title compound (31.57 g, 47%) as a colorless powder. Anal calcd for $C_{14}H_{23}NO_4.\frac{1}{4}H_2O$: C, 61.40; H, 8.65; N, 5.11. Found: C, 61.38; H, 8.54; N, 5.22. MS M+1 calcd for $C_{14}H_{23}NO_4$ 270, found 270. DSC=102.3°–106.4° C. at 101.7 J/g. Chromatography of the mother liquor on silica gel eluting with EtOH/$CH_2Cl_2$/HOAc (2/98/1) gave an additional 17.5 g (26%) of the title compound.

EXAMPLE G

Preparation of 1,1-Dimethylethyl 2,5-dihydro-4-hydroxy-5-oxo-1-phenyl-1H-pyrrole-3-carboxylate To a solution of the title compound of Example B (29.37 g, 0.133 mol) and di-tert-butyl oxalate (26.90 g, 0.133 mol) in dry THF (350 ml) was added potassium tert-butoxide (29.84 g, 0.266 mol) and the resulting solution was heated under reflux for 24 h. The mixture was then cooled and the solvent removed in vacuo. The resulting solid was suspended in $CH_2Cl_2$ and 1N aqueous HCl was added. The resulting suspension was filtered and the organic filtrate was dried over $MgSO_4$ and concentrated in vacuo. The residue was then chromatographed on silica gel eluting with 1/1/98 HOAc/EtOH/$CH_2Cl_2$ to give the title compound (19.06 g, 52%) as a solid. Anal calcd for $C_{15}H_{17}NO_4$: C, 65.44; H, 6.22; N, 5.09. Found: C, 65.05; H, 6.33; N, 4.86. MS M+1 calcd for $C_{15}H_{17}NO_4$ 276, found 276.

EXAMPLE H

Preparation of 1,1-Dimethylethyl 1-(2-fluorophenyl)-2,5-dihydro-4-hydroxy-5-oxo-1H-pyrrole-3-carboxylate To a solution of the title compound of Example C (5.41 g, 22.6 mmol) in dry THF (100 ml) was added di-tert-butyl oxalate (4.57 g, 22.6 mmol), followed by potassium tert-butoxide (5.07 g, 45.2 mmol) and the resulting dark yellow solution was stirred for 84 h at room temperature. The reaction mixture was then acidified with 1N HCl to pH=3, followed by the addition of $H_2O$ (35 ml) and the mixture was then extracted with $CH_2Cl_2$. The combined organic layers were dried with $MgSO_4$, filtered and dried to give a solid which was chromatographed on silica gel eluting with 1/1/98 MeOH/HOAc/$CH_2Cl_2$ to give the title compound (3.166 g, 48%). Anal calcd for $C_{15}H_{16}NO_4F$: C, 61.43; H, 5.50; N, 4.78. Found: C, 61.16; H, 5.50; N, 4.77.

EXAMPLE I

Preparation of 1,1-Dimethylethyl 2,5-dihydro-4-hydroxy-5-oxo-1-(phenylmethyl)-1H-pyrrole-3-carboxylate To a solution of benzyl amine (7.3 ml, 0.067 mol) in dry EtOH (freshly distilled fromسodium) was added tert-butyl acrylate (6.8 ml, 0.046 mol) via syringe and the resulting solution was stirred under an atmosphere of argon for 64 h at room temperature. To the solution was then added diethyl oxalate (9.90 g, 0.068 mol). The solution was then cooled to 0° C. and a freshly prepared solution of sodium ethoxide [freshly prepared from sodium (1.7 g, 0.074 mol) and 75 ml of EtOH]was added via cannula while maintaining the temperature between 0° C. and 5° C. After the addition was complete the solution was warmed to room temperature and stirred overnight. To the resulting slurry was added 100 ml of water followed by the slow addition of 30% aqueous HCl to acidify to pH=1. The suspension was then extracted with $CH_2Cl_2$. The organic phase was dried over $MgSO_4$, filtered, and concentrated in vacuo to give the title compound as a light pink powder (8.37 g, 62.9%). Purification of an analytical sample by chromatography on silica gel eluting with 5/94.5/0.5 MeOH/$CH_2Cl_2$/HOAc gave 8.67g, (65%) of the title compound as a powder. Anal calcd for $C_{16}H_{19}NO_4$: C, 66.43; H, 6.52; N, 4.84. Found: C, 66.38; H, 6.70; N, 5.10. DSC=172.2°–176.2° at 190.9 J/g.

EXAMPLE J

Preparation of Ethyl 2,5-dihydro-4-hydroxy-2-methyl-5-oxo-1-pentyl-1H-pyrrole-3-carboxylate To a solution of n-pentyl amine (28.98 ml, 0.25 mol) in absolute EtOH (110 ml) was added ethyl crotonate (31.1 ml, 0.25 mol) and the solution was stirred for 16 h at room temperature. To the clear solution was then added diethyl oxalate (33.95 ml, 0.25 mol) followed by a solution of sodium ethoxide [freshly prepared from sodium (5.75 g, 0.25 mol) and 75 ml of absolute EtOH]. After stirring for 16 h at room temperature, the solvent was removed in vacuo to give an orange oil. Water was added to the oil followed by 1N HCl to acidify to pH=3, and the mixture was then extracted with $CH_2Cl_2$ (3×500 ml). The combined organic layers were washed with water and brine and then concentrated in vacuo to give an oil which was chromatographed on silica gel eluting with 10/89/1 EtOH/$CH_2Cl_2$/HOAc to give the title compound (21.88 g, 34%) as a pink solid. DSC=37.8°–44.3° C. at 63.9 J/g.

EXAMPLE K

Preparation of Ethyl 4-(hydroxyimino)-5-oxo-1-pentyl-3-pyrrolidinecarboxylate

To a solution of the title compound of Example D (5.0 g, 20.2 mmol) in 50 ml of pyridine was added hydroxylamine hydrochloride (1.58 g, 24.2 mmol) and the solution was stirred for 16 h at room temperature. Concentration in vacuo gave an oil which was chromatographed on silica gel eluting with EtOH/$CH_2Cl_2$ (10/90) to give the title compound (5.18 g, 98%) as a colorless solid. MS calcd for $C_{12}H_{20}N_2O_4$ 256, found 256.

EXAMPLE L

Preparation of Ethyl 4-(hydroxyimino)-5-oxo-1-phenyl-3-pyrrolidinecarboxylate

To a mechanically stirred solution of the title compound of Example E (21 g, 0.085 mol) in 450 ml of pyridine was added hydroxylamine hydrochloride (8.83 g, 0.127 mol). After stirring for 4 days at room temperature the solution was concentrated in vacuo to give a solid which was chromatographed on silica gel eluting with 3% EtOH/$CH_2Cl_2$ to give the title compound (13.71 g, 61%) as a colorless powder. Anal calcd for $C_{13}H_{14}N_2O_4$: C, 59.53; H, 5.40; N, 10.68. Found: C, 59.48; H, 5.47; N, 10.64. MS calcd for $C_{13}H_{14}N_2O_4$ 262, found 262. DSC=153.2°–155.4° C. at 91.1 J/g.

EXAMPLE M

Preparation of 1,1-Dimethylethyl 4-(hydroxyimino)-5-oxo-1-pentyl-3-pyrrolidine carboxylate To a mechanically stirred solution of the title compound of Example F (17.5 g, 0.065 mol) in 60 ml of pyridine was added hydroxylamine hydrochloride (5.41 g, 0.078 mol) and resulting solution was stirred for 36 h. Evaporation of the solvent afforded a light yellow oil which was chromatographed on silica gel eluting with 3% EtOH/$CH_2Cl_2$ to give the title compound (16.48 g, 89%) as a white solid: Anal calcd for $C_{14}H_{24}N_2O_4$: C, 59.14, H, 8.51; N, 9.85. Found C, 58.91; H, 8.48; N, 9.71. MS calcd for $C_{14}H_{24}N_2O_4$ 284, found 284. DSC=131.0°–134.7° C. at 93.1 J/g.

EXAMPLE N

Preparation of 1,1-Dimethylethyl 4-(hydroxyimino)-5-oxo-1-phenyl-3-pyrrolidine carboxylate To a solution of the title compound of Example G (9.2 g, 0.033 mol) in pyridine (100 ml) was added hydroxylamine hydrochloride (11.62 g, 0.167 mol) and the resulting solution was stirred at room temperature for 4 days. Concentration in vacuo gave a solid which was purified on a Waters Prep 500A eluting with 5/95 EtOH/$CH_2Cl_2$ to afford the title compound (3.08 g, 32%) as a solid. DSC=187.8°–190.8° C. at 378.5 J/g.

EXAMPLE O

Preparation of 1,1-Dimethylethyl 1-(2-fluorophenyl)-4-(hydroxyimino)-5-oxo-3-pyrrolidinecarboxylate To a solution of the title compound of Example H (3.16 g, 10.8 mmol) in pyridine (50 ml) was added hydroxylamine hydrochloride (3.73 g, 54. mmol) and the reaction was stirred for 5 days(d) at room temperature. After the reaction was concentrated in vacuo, HO was added and the mixture was extracted with $CH_2Cl_2$. Drying of the organic phase ($MgSO_4$) and concentration gave a solid which was chromatographed on silica gel eluting with 2% EtOH/$CH_2Cl_2$ to give the title compound (1.91 g, 57%). Anal calcd for $C_{15}H_{17}N_2O_4F$: C, 58.44; H, 5.56; N, 9.09. Found: C, 58.43; H, 5.62; N, 8.75. DSC=175.1°–180.2° C. at 225.6 J/g.

EXAMPLE P

Preparation of 1,1-Dimethylethyl 4-(hydroxyimino)-5-oxo-1-(phenylmethyl)-3-pyrrolidinecarboxylate To a solution of the title compound of Example I (8.07 g, 27.9 mmol) in 150 ml of pyridine was added hydroxylamine hydrochloride (9.69 g, 139 mmol) and resulting solution was stirred for 4 d. Addition of $H_2O$ resulted in the formation of precipitate which was filtered to give the title compound (7.11 g, 84%) as a colorless solid. Calculated for $C_{16}H_{20}N_2O_4\cdot\frac{1}{2}H_2O$: C, 61.35; H, 6.76; N, 8.94. Found C, 61.35; H, 6.57, N, 9.34.

EXAMPLE Q

Preparation of Ethyl 4-(hydroxyimino)-2-methyl-5-oxo-1-pentyl-3-pyrrolidinecarboxylate To the title compound of Example J (21.6 g, 0.085 mol) in pyridine (150 ml) was added hydroxylamine hydrochloride (10.6 g, 0.17 mol) and the solution was stirred for 5 days. The solvent was removed in vacuo to give an orange oil which as chromatographed on silica gel eluting with 2% EtOH/$CH_2Cl_2$ to give the title compound (13.67 g, 59%) as an oil. Calculated $C_{13}H_{22}N_2O_4\cdot\frac{1}{2}H_2O$: C, 55.90; H, 8.30; N, 10.02 Found: C, 55.99; H, 8.38; N, 10.00. MS calcd for $C_{13}H_{22}N_2O_4$ 270, found 270.

EXAMPLE R

Preparation of Ethyl 4-amino-5-oxo-1-pentyl-3-pyrrolidinecarboxylate

A solution of the title compound of Example K (1.0 g, 3.9 mmol) in 50 ml EtOH was hydrogenated with 10% palladium on carbon at 60 psi at 60° C. for 18 h. Filtration and evaporation of the solvent gave an oil which was chromatographed on silica gel eluting with EtOH/$CH_2Cl_2$ (5/95) to give the title compound (382 mg, 40%) as a colorless solid. $^1$H NMR (300 MHz, $CDCl_3$) δ4.20 (2H, q), 3.80 (1H, d), 3.59 (1H, td), 3.48 (1H, q), 3.35 (1H, m), 3.29 (2H, m), 1.69 (2H, br s), 1.52 (2H, m), I.32 (4H, m), 1.30 (3H, t), 0.90 (3H, t).

EXAMPLE S

Preparation of Ethyl 4-amino-5-oxo-1-phenyl-3-pyrrolidinecarboxylate

A solution of oxime of Example L (791 mg, 3.01 mmol) in 50 ml of EtOH was hydrogenated with Raney nickel in a 150 ml Parr bomb with 1,000 psi of hydrogen at 50° C. for 4h. The solution was then filtered to remove the catalyst and the solution was concentrated in vacuo. The resulting oil was radially chromatographed on silica gel eluting with 7% EtOH/$CH_2Cl_2$ to give the title compound (342 mg, 44%). DSC=190.3°–193.8° C. at 71.1 J/g.

EXAMPLE T

Preparation of 1,1-Dimethylethyl 4-amino-5-oxo-1-pentyl-3-pyrrolidinecarboxylate A solution of oxime of Example M (20.0 g, 68.6 mmol) in 200 ml of EtOH was hydrogenated with 10% palladium on carbon at 1200 psi at 70° C. for 24 h. Filtration and evaporation of the solution gave the title compound (18.5 g, 100%) as colorless, low-melting solid. MS calcd for $C_{14}H_{26}N_2O_3$ 270, found 270. $^1$H NMR (300 MH$_z$,$CDCl_3$) δ3.63 (1H, d), 3.50 (1H, m), 3.41 (1H, m), 3.25 (2H, m), 1.72 (2H, s), 1.52 (1H, m), 1.47 (9H, s), 1.29 (4H, m), 0.89 (2H, t).

EXAMPLE V

Preparation of 1,1-Dimethylethyl 4-amino-5-oxo-1-phenyl-3-pyrrolidinecarboxylate A solution of oxime of Example N (3.08 g, 10.6 mmol) in EtOH (80 ml) was hydrogenated at 1000 psi at 70° C. on 10% palladium on carbon. Filtration and concentration of the filtrate gave an oil which was chromatographed on silica gel eluting with 2/97.75/0.25 EtOH/$CH_2Cl_2$/$NH_4OH$ to afford the title compound (1.76 g, 60%) as a white solid. Anal calcd for $C_{15}H_{20}N_2O_3$: C, 65.20; H, 7.30; N, 10.14. Found: C, 64.95; H, 7.39; N, 10.04. MS Calcd for $C_{15}H_{20}N_2O_3$ 276, found 276. DSC=105.0°–121.1° at 57.2 J/g.

EXAMPLE W

Preparation of 1,1-Dimethylethyl 4-amino-1-(2-fluorophenyl)-5-oxo-3-pyrrolidinecarboxylate A solution of oxime of Example 0 (1.23 g, 3.99 mmol) in EtOH was hydrogenated at 1000 psi on Pd/C at 70° C. for 24 h. The solvent was removed in vacuo to give an oil which was chromatographed on silica gel eluting with 2% EtOH/$CH_2Cl_2$ to give the title compound (850 mg, 72%) as a solid. Anal calcd for $C_{15}H_{19}N_2O_3F$: C, 61.21; H, 6.51; N, 9.52; F, 6.45. Found: C, 60.87; H, 6.61;

N, 9.32; F, 6.10. MS calcd for $C_{15}H_{19}N_2O_3F$ 294, found 294. DSC=71.2°–74.9° C. at 76.6 J/g.

EXAMPLE X

Preparation of 1,1-Dimethylethyl 4-amino-5-oxo-1-(phenylmethyl)-3-pyrrolidinecarboxylate A solution of 2.014g (6.6 mmol) of the oxime of Example P in EtOH (400 ml) was hydrogenated with 4% palladium on carbon at 1000 psi at 70° C. for 24 h. Filtration and evaporation of the filtrate gave a white solid which was chromatographed on silica gel eluting with 3% $CH_3OH/CH_2Cl_2/1\%$ $NH_4OH$ to give the title compound (997 mg, 52%). Anal. calcd. for $C_{16}H_{22}N_2O_3\cdot\frac{1}{2}H_2O$: C, 64.19; H, 7.74; N, 9.36 Found: C, 64.36; H, 7.71; N, 9.41.

EXAMPLE Y

Preparation of Ethyl 4-amino-2-methyl-5-oxo-1-pentyl-3-pyrrolidinecarboxylate

A solution of oxime of Example Q in EtOH is hydrogenated with 10% palladium on carbon at 1200 psi at 70° C. for 24 h. Filtration and evaporation of the filtrate gives a residue which is chromatographed on silica gel eluting with 2% $EtOH/CH_2Cl_2$ to give the title compound.

TABLE A

Examples 1 to 26 Have The Following Structures

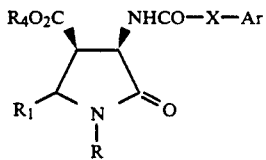

| Ex | R | $R_1$ | $R_4$ | X | Ar |
|---|---|---|---|---|---|
| 1 | n-pentyl | H | Et | bond | 3-quinolinyl |
| 2 | phenyl | H | t-Bu | bond | " |
| 3 | 2-F-phenyl | H | t-Bu | bond | " |
| 4 | phenyl | H | Et | bond | 2-indolyl |
| 5 | phenyl | H | t-Bu | bond | " |
| 6 | benzyl | H | t-Bu | bond | " |
| 7 | n-pentyl | Me | Et | bond | " |
| 8 | phenyl | H | Et | $CH_2$ | 3-indolyl |
| 9 | pentyl | H | t-Bu | bond | 3,4-dichlorophenyl |
| 10 | pentyl | H | t-Bu | NH | " |
| 11 | phenyl | H | Et | bond | " |
| 12 | phenyl | H | Et | NH | " |
| 13 | phenyl | H | t-Bu | O | " |
| 14 | benzyl | H | t-Bu | bond | " |
| 15 | benzyl | H | t-Bu | NH | " |
| 16 | n-pentyl | H | Et | bond | 2-naphthyl |
| 17 | n-pentyl | H | t-Bu | NH | " |
| 18 | phenyl | H | Et | bond | " |
| 19 | phenyl | H | t-Bu | bond | " |
| 20 | 2-F-phenyl | H | t-Bu | bond | " |
| 21 | benzyl | H | t-Bu | bond | " |
| 22 | n-pentyl | H | t-Bu | bond | 4-chlorophenyl |
| 23 | phenyl | H | Et | bond | " |
| 24 | n-pentyl | H | Et | NH | " |
| 25 | phenyl | H | t-Bu | bond | 3-indazolyl |
| 26 | phenyl | H | t-Bu | bond | 2-pyrazinyl |

EXAMPLE 1

Preparation of Ethyl cis-5-oxo-1-pentyl-4-[(3-quinolinylcarbonyl)amino]-3-pyrrolidinecarboxylate To quinoline-3-carboxylic acid (100 mg, 0.578 mmol) suspended in $CH_2Cl_2$ was added 2 drops of dimethylformamide followed by the dropwise addition of oxalyl chloride (0.1 ml, 1.15 mmol). After stirring for 2 h at room temperature the solution was evaporated to dryness to give the acid chloride. The acid chloride was then redissolved in $CH_2Cl_2$ and syringed dropwise into a solution of the aminopyrrolidinone of Example R (140 mg, 0.578 mmol) with triethylamine (0.4 ml, 2.89 mmol) in $CH_2Cl_2$. After stirring for 12 h at room temperature the reaction mixture was evaporated in vacuo to give an oil which was chromatographed on silica gel eluting with $EtOH/CH_2Cl_2$ (2%–5%) to give the title compound (173 mg, 75%) as a colorless solid. MS calcd for $C_{22}H_{27}N_3O_4$ 397, found 397.

EXAMPLE 2

Preparation of 1,1-Dimethylethyl cis-5-oxo-1-phenyl-4-[(3-quinolinylcarbonyl)amino]-3-pyrrolidinecarboxylate To a solution of 3-quinolinecarboxylic acid (118 mg, 0.68 mmol) in $CH_2Cl_2$ (3 ml) was added oxalyl chloride (0.12 ml, 1.36 mmol) and the resulting solution was stirred for 2.5 h at room temperature. The solvent was removed in vacuo and the acid chloride was redissolved in $CH_2Cl_2$ (3 ml) to which was added the aminopyrrolidinone of Example V (200 mg, 0.68 mmol) and triethylamine (344 mg, 3.4 mmol) in $CH_2Cl_2$ (3 ml). After stirring for 18 h at room temperature, the solvent was removed in vacuo and the resulting oil was purified by radial chromatography on a silica gel plate eluting with 2% $EtOH/CH_2Cl_2$ to give the title compound (223 mg, 73%) as a solid. $^1H$ NMR (300 MHz, $CDCl_3$) δ9.38 (1H, d), 8.68 (1H, d), 8.18 (1H, d), 7.94 (1H, d), 7.85 (1H, t), 7.64 (2H, d), 7.58 (1H, m), 7.42 (2H, t), 7.21 (1H, t),5.23 (1H, t), 4.15 (1H, m), 4.06 (1H, d), 3.81 (1H, t), 1.38 (9H, s).

EXAMPLE 3

Preparation of 1,1-Dimethylethyl cis-1-(2-fluorophenyl)-5-oxo-4-[(3-quinolinylcarbonyl)amino]-3-pyrrolidinecarboxylate To a solution of 3-quinolinecarboxylic acid (118 mg, 0.68 mmol) in $CH_2Cl$ (3 ml) was added oxalyl chloride (0.12 ml, 1.36 mmol) and the solution was stirred for 2.5 h. Removal of the solvent in vacuo gave a colorless solid which was redissolved in $CH_2Cl_2$ (3 ml). To this solution was added a solution of aminopyrrolidinone of Example W (200 mg, 0.68 mmol) and triethylamine (344 mg, 3.4 mmol) in $CH_2Cl_2$ (3 ml) and the resulting solution was stirred for 18 h. Removal of the solvent in vacuo and purification of the resulting solid via radial chromatography (4 mm plate) eluting with 2% $EtOH/CH_2Cl_2$ gave the title compound (223 mg, 73%) as a solid. $^1H$ NMR (300 MHz, $CDCl_3$) δ9.35 (1H, d), 8.68 (1H, d), 8.19 (1H, d), 7.94 (1H, d), 7.84 (1H t), 7.64 (1H, t), 7.54 (1H, t), 7.32 (1H, m), 7.19 (2H, m), 5.28 (1H, t), 4.21 (1H, m), 3.91 (1H, d), 3.78 (1H, q), 3.49 (1H, s), 1.41 (9H, s).

EXAMPLE 4

Preparation of Ethyl cis-4-[(1H-indol-2-ylcarbonyl)amino]-5-oxo-1-phenyl-3-pyrrolidinecarboxylate To indole-2-carboxylic acid (65 mg, 0.4 mmol) suspended in $CH_2Cl_2$ was added 2 drops of dimethylformamide followed by the dropwise addition of oxalyl chloride (0.07 ml, 0.8 mmol). After stirring for 2 h at room temperature the solution was evaporated to dryness to give the acid chloride. The acid chloride was then redissolved in CH₂Cl₂ and syringed dropwise into a solution of the aminopyrrolidinone of Example S (100 mg, 0.4 mmol) with triethylamine (0.3 ml, 2.0 mmol) in CH₂Cl₂. After stirring for 12 h at room temperature the reaction mixture was evaporated in vacuo to give an oil which was chromatographed on silica gel eluting with EtOH/CH₂Cl₂ 2%-5%) to give the title compound (68 mg, 43%) as a colorless solid. $^1$NMR (300 MHz, CDCl₃) δ9.09 (1H, br s), 7.66 (4H, m), 7.43 (4H, t), 7.16 (1H, m), 6.99 (2H, m), 5.21 (1H, t), 4.14 (4H, m), 4.05 (1H, m), 3.85 (1H, t), 1.14 (3H, t).

EXAMPLE 5

Preparation of 1,1-Dimethylethyl cis-4-[(1H-indol-2-ylcarbonyl)amino]-5-oxo-1-phenyl-3-pyrrolidinecarboxylate To a solution of indole-2-carboxylic acid (103 mg, 0.64 mmol) in dry DMF (1.5 ml) was added 1,1-carbonyldiimidazole (104 mg, 0.64 mmol) and the resulting solution was stirred for 2.5 h at room temperature. To this mixture was then added a solution of aminopyrrolidinone of Example V (177 mg, 0.64 mmol) in dry DMF (1.5 ml). This solution was then stirred for 18 h at room temperature after which time the solvent was removed in vacuo giving an oil. Chromatography of the oil on a silica gel chromatotron plate (2 mm) eluting with 2/98 EtOH/CH₂Cl₂ gave the title compound (110 mg, 49%) as a solid. $^1$NMR (300 MHz, CDCl₃) δ9.17 (1H, s), 7.66 (2H, m), 7.43 (2H, t), 7.32 (1H, t), 7.16 (2H, m), 6.98 (2H, m), 5.18 (1H, q), 4.42 (1H, t), 4.10 (2H, m), 3.76 (1H, t), 1.36 (9H, s).

EXAMPLE 6

Preparation of 1,1-Dimethylethyl cis-4-[(1H-indol-2-ylcarbonyl)amino]-5-oxo-1-phenyl-methyl)-3-pyrrolidinecarboxylate To a solution of indole-2-carboxylic acid (183 mg, 1.1 mmol) in DMF was added 1,1-carbonyldiimidazole (84 mg, 1.1 mmol). After stirring for 5 h at room temperature a solution of the aminopyrrolidinone of Example X (330 mg 1.1 mmol) in DMF was added. After stirring for 12 h at room temperature the reaction mixture was evaporated in vacuo to give an oil which was chromatographed on silica gel eluting with EtOH/CH₂Cl₂ (2%-5%) to give 350 mg (73%) of the title compound. MS calcd for C₃₅H₂₇N₃O₄ 433, found 433.
DSC=206.10°-211.61° C. at 90.50 J/g 217.23° C. at 63.56 J/g.

EXAMPLE 7

Preparation of Ethyl cis-4-[(1H-indol-2-ylcarbonyl)amino]-2-methyl-5-oxo-1-pentyl-3-pyrrolidinecarboxylate To indole-2-carboxylic acid (0.264 mg, 1.6 mmol) in DMF (3 ml.) was added 1,1-carbonyldiimidazole (260 mg, 1.6 mmol). After stirring for 4 h at room temperature a solution of the aminopyrrolidinone of Example Y (408 mg, 1.6 mmol) in DMF was added. After stirring for 24 h at room temperature the reaction mixture was evaporated in vacuo to give an oil which was chromatographed on silica gel eluting with EtOH/CH₂Cl₂ (2%-5%) to give the title compound, 600 mg (95%). $^1$NMR (300 MHz, CDCl₃) δ0.98 (t, 3H), 3.75 (m, 1H), 3.96 (m, 1H), 4.02 (m, 2H), 4.19 (m, 1H), 5.15 (t, 1H), 7.04 (t, 1H), 7.27 (m, 2H), 7.43 (t, 2H), 7.61 (d, 1H), 7.72 (d, 1H), 8.99 (d, 1H).

EXAMPLE 8

Preparation of Ethyl cis-4-[(1H-indol-3-ylacetyl)amino]-5-oxo-1-phenyl-3-pyrrolidinecarboxylate To a solution of indole-3-acetic acid (248 mg, 1.42 mmol) in DMF (3 ml) was added 1,1-carbonyldiimidazole (230 mg, 1.42 mmol). After stirring for 2 h a solution of the aminopyrrolidinone of Example S (352 mg, 1.42 mmol) in DMF (1 ml) was added. After stirring for an additional 18 h the solvent was evaporated to give an oil which was chromatographed on silica gel eluting with EtOH/CH₂Cl₂ (2%-5%) to give 470 mg (91%) of the title compound as a solid. NMR (DMSO) 400 MHz: 3.25δ, m, 1H; 3.59δ, d, 2H; 3.88δ, t, 1H; 4.01δ, t, 1H; 4.65δ, q, 1H; 6.98δ, t, 1H; 7.08δ, t, 1H; 7.15δ, t, 1H; 7.24δ, d, 1H; 7.37, m, 3H; 7.56δ, d, 1H; 7.78δ, d, 2H; 8.62δ, d, 1H.

EXAMPLE 9

Preparation of 1,1-Dimethylethyl cis-4-[[(3,4-dichlorophenyl)carbonyl]amino]-5-oxo-1-pentyl-3-pyrrolidinecarboxylate To a solution of the aminopyrrolidinone of Example T (110 mg, 0.407 mmol) and triethylamine (0.11 ml, 0.814 mmol) in CH₂Cl₂ was added a solution of 3,4-dichlorobenzoyl chloride (85 mg, 0.407 mmol) in CH₂Cl₂ dropwise via syringe. After stirring for 12 h at room temperature the reaction mixture was evaporated in vacuo to give an oil which was chromatographed on silica gel eluting with EtOH/CH₂Cl₂ (2%-5%) to give the title compound (150 mg, 85%) as a colorless solid. DSC=108.1-111.3 at 38.5 J/g. Anal calcd for C₂₁H₂₈N₂O₄Cl₂: C, 56.89; H, 6.36; N, 6.32. Found C, 57.09; H, 5.87; N, 6.22. MS calcd for C₂₁H₂₈N₂O₄Cl₂ 443, found 443.

EXAMPLE 10

Preparation of 1,1-Dimethylethyl cis-4-[[[(3,4-dichlorophenyl)amino]carbonyl]amino]-5-oxo-1-pentyl-3-pyrrolidinecarboxylate To a solution of 3,4-dichlorophenyl isocyanate (76 mg, 0.407 mmol) dissolved in 3 ml of CH₂Cl₂ was added a solution of aminopyrrolidinone of Example T (110 mg, 0.407 mmol) in 3 ml of CH₂Cl₂ and the resulting solution was stirred for 16 h at room temperature. Evaporation of the solvent in vacuo gave a solid which was purified on silica gel eluting with 5/95 EtOH/CH₂Cl₂ to give the title compound (167 mg, 90%) as a colorless solid. DSC=162.0°-164.2° C. at 65.0 J/g. MS calculated for C₂₁H₂₉N₃O₄Cl₂ 458, found 458.

EXAMPLE 11

Preparation of Ethyl cis-4-[[(3,4-dichlorophenyl)carbonyl]amino]-5-oxo-1-phenyl-3-pyrrolidinecarboxylate To a solution of 3,4-dichlorobenzoyl chloride (295 mg, 1.41 mmol) in CH₂Cl₂ (4 ml) was added a solution of aminopyrrolidinone of Example S (350 mg, 1.41 mmol) and triethylamine (0.4 ml, 2.82 mmol) in CH₂Cl₂ (4 ml) and the resulting solution was stirred for 18 h at room temperature. Concentration in vacuo gave an oil which was chromatographed on silica gel eluting with 2% EtOH/CH$_2$Cl$_2$ to give the title compound (400 mg, 67%) as a colorless solid. Anal calcd for C$_{20}$H$_{18}$N$_2$O$_4$Cl$_2$: C, 57.02; H, 4.31; N, 6.65. Found: C, 57.05; H, 4.39; N, 6.50. MS M+1 calcd for C$_{20}$H$_{18}$N$_2$O$_4$Cl$_2$ 422, found 422.
DSC=185.5°–193.1° C. at 82.8 J/g.

EXAMPLE 12

Preparation of Ethyl cis-4-[[[(3,4-dichlorophenyl)amino]carbonyl]amino]-5-oxo-1-phenyl-3-pyrrolidinecarboxylate To a solution of 3,4-dichlorophenylisocyanate in CH$_2$Cl$_2$ (3 ml) was added a solution of aminopyrrolidinone of Example S (350 mg, 1.41 mmol) in CH$_2$Cl$_2$ (3 ml) and the resulting solution was stirred for 18 h at room temperature. Concentration in vacuo gave a solid which was triturated with CH$_2$Cl$_2$ and filtered to give the title compound (420 mg, 68%) as a solid. MS M+1 calcd for C$_{20}$H$_{19}$N$_3$O$_4$Cl$_2$ 437, found 437. DSC=249.1°–251.7° C. at 112.7 J/g.

EXAMPLE 13

Preparation of 1,1-Dimethylethyl cis-4-[[(3,4-dichlorophenoxy)carbonyl]amino]-5-oxo-1-phenyl-3-pyrrolidinecarboxylate To a cooled (0° C.) solution of aminopyrrolidinone of Example V (300 mg, 1.09 mmol) and triethylamine (0.15 mL, 1.09 mmol) in CH$_2$Cl$_2$ is added 3,4-dichlorophenyl chloroformate (207 mg, 1.09 mmol). After warming to room temperature the reaction is stirred for 12 h. The reaction mixture is then washed with water and brine, dried (MgSO$_4$) and concentrated in vacuo to give a residue which is chromatographed on silica gel eluting with EtOH/CH$_2$Cl$_2$ (2%–5%) to give the title compound.

EXAMPLE 14

Preparation of 1,1,-Dimethylethyl cis-4-[[(3,4dichlorophenyl)carbonyl]amino]-5-oxo-1-phenylmethyl-3-pyrrolidinecarboxylate To a solution of 3,4 dichlorobenzoyl chloride (419 mg, 2.0 mmol) in CH$_2$Cl$_2$ (3 ml) was added a solution of aminopyrrolidinone of Example X (286 mg, 0.99 mmol) and triethylamine (0.28 ml, 2.0 mmol) in CH$_2$Cl$_2$ (3 ml). After stirring for 18 h at room temperature the reaction mixture was evaporated in vacuo to give a solid which was chromatographed on silica gel eluting with 2% EtOH/CH$_2$Cl$_2$ to give 352 mg (77%) of the title compound.
Anal calcd for C$_{23}$H$_{24}$N$_2$O$_4$Cl$_2$: C, 59.62; H, 5.22; N, 6.05. Found C, 59.20; H, 5.31; N, 5.90. DSC=132.64°–140.52° C. at 50.30 J/g.

EXAMPLE 15

Preparation of 1,1-dimethylethyl cis-4-[[[(3,4-dichlorophenyl)amino]carbonyl]amino]-5-oxo-1-(phenylmethyl)-3-pyrrolidinecarboxylate To a solution of 3,4-dichlorophenyl isocyanate (194 mg, 1.0 mmol) in CH$_2$Cl$_2$ (3 ml) was added aminopyrrolidinone of Example X (300 mg, 1.0 mmol) in CH$_2$Cl$_2$ (2 ml). After stirring for 48 h the solvent was concentrated in vacuo to give a solid which was chromatographed on silica gel eluting with 5% EtOH/CH$_2$Cl$_2$ to give 425 mg (89%) of the title compound.

Anal Calcd for C$_{23}$H$_{25}$N$_3$O$_4$Cl$_2$: C, 57.75; H, 5.27; N, 8.78; Cl, 14.82. Found C, 57.93; H, 5.38; N, 8.65; Cl, 14.97. DSC=188.62° C.–190.68° C. at 78.73 J/g.
MS calcd for C$_{23}$H$_{25}$N$_3$O$_4$Cl$_2$ 478, found 478.

EXAMPLE 16

Preparation of Ethyl cis-4-[(2-naphthalenylcarbonyl)amino]-5-oxo-1-pentyl-3-pyrrolidinecarboxylate To a solution of the aminopyrrolidinone of Example R (120 mg, 0.495 mmol) and triethylamine (0.35 ml, 2.48 mmol) in CH$_2$Cl$_2$ was added a solution of 2-naphthoyl chloride (94 mg, 0.495 mmol) in CH$_2$Cl$_2$ dropwise via syringe. After stirring for 12 h at room temperature the reaction mixture was evaporated in vacuo to give a residue which was chromatographed on silica gel eluting with EtOH/CH$_2$Cl$_2$ (2%–5%) to give the title compound (172 mg, 69%) as a colorless solid. MS M+1 calcd for C$_{23}$H$_{28}$N$_2$O$_4$ 397; found 397.

EXAMPLE 17

Preparation of 1,1-Dimethylethyl cis-4-[[(2-naphthalenylamino)carbonyl]amino]-5-oxo-1-pentyl-3-pyrrolidinecarboxylate To a solution of 2-naphthyl isocyanate (69 mg, 0.407 mmol) dissolved in 3 ml of CH$_2$Cl$_2$ was added a solution of the amine of Example T (110 mg, 0.407 mmol) in 3 ml of CH$_2$Cl$_2$ and the resulting solution was stirred for 16 h at room temperature. Evaporation of the solvent in vacuo gave a solid which was purified on silica gel eluting with 5/95 EtOH/CH$_2$Cl$_2$ to give the title compound (130 mg, 73%) as a colorless solid. MS calcd for C$_{23}$H$_{33}$N$_3$O$_4$ 439, found 439.

EXAMPLE 18

Preparation of Ethyl cis-4-[(2-naphthalenylcarbonyl)amino]-5-oxo-1-phenyl-3-pyrrolidinecarboxylate To a solution of the aminopyrrolidinone of Example S (1.54 g, 6.2 mmol) and triethylamine (1.3 ml, 9.3 mmol) in CH$_2$Cl$_2$ (10 ml) was added a solution of 2-naphthoyl chloride (1.18 g, 6.2 mmol) in CH$_2$Cl$_2$ (7 ml) dropwise via syringe. After stirring for 12 h at room temperature the reaction mixture was evaporated in vacuo to give a residue which was chromatographed on silica gel eluting with EtOH/CH$_2$Cl$_2$ (2%–5%) to give the title compound (2.5 g, 100%) as a colorless solid. Anal calcd for C$_{24}$H$_{22}$N$_2$O$_4$: C, 71.63; H, 5.51; N, 6.96. Found C, 71.31; H, 5.45; N, 6.73. MS calcd for C$_{24}$H$_{22}$N$_2$O$_4$ 402; found 402.

EXAMPLE 19

Preparation of 1,1-Dimethylethyl cis-4-[(2-naphthalenylcarbonyl)amino]-5-oxo-1-phenyl-3-pyrrolidinecarboxylate To a solution of 2-naphthoyl chloride (1.20 g, 6.29 mmol) in CH$_2$Cl$_2$ (9 ml) was added a solution of aminopyrrolidinone of Example V (1.56 g, 5.64 mmol) and triethylamine (1.31 ml, 9.43 mmol) in CH$_2$Cl$_2$ (10 ml) and the resulting solution was stirred for 60 h at room temperature. After removing the solvent in vacuo, H$_2$O was added and the mixture was extracted with CH$_2$Cl$_2$. The combined organic layers were washed with brine, dried (MgSO$_4$), filtered and concentrated under reduced pressure to give a solid which was chromatographed on silica gel eluting with 2% EtOH/CH$_2$Cl$_2$ to give the title compound (2.28 g, 94%) as a colorless solid. Anal calcd for $C_{26}H_{26}N_2O_4 \cdot 2/3H_2O$: C, 70.57; H, 5.92; N, 6.33. Found: C, 70.36; H, 6.16; N, 6.23. MS calcd for $C_{26}H_{26}N_2O_4$ 430, found 430. DSC =182.4°-185.1° C. at 107.4 J/g.

EXAMPLE 20

Preparation of 1,1-Dimethylethyl cis-1-(2-fluorophenyl)-4-[(2-naphthalenylcarbonyl)amino]-5-oxo-3-pyrrolidinecarboxylate To a solution of 2-naphthoyl chloride (178 mg, 0.934 mmol) in $CH_2Cl_2$ (3 ml) was added a solution of aminopyrrolidinone of Example W (250 mg, 0.849 mmol) and triethylamine (146 mg, 1.44 mmol) in $CH_2Cl_2$ (3 ml) and the resulting solution was stirred at room temperature for 18 h. The solvent was then removed in vacuo and the resulting foam was purified by radial chromatography on a silica gel plate (4 mm) eluting with 2/98 $EtOH/CH_2Cl_2$ to give the title compound (380 mg, 100%) as a colorless foam. MS M+1 calcd for $C_{26}H_{25}N_2O_4F$ 449, found 449. DSC =142.2°-151.5° C.@55.9 J/g.

EXAMPLE 21

Preparation of 1,1-dimethylethyl cis-4-[(2-naphthalenylcarbonyl)amino]-5-oxo-1-(phenylmethyl)-3-pyrrolidinecarboxylate To a solution of 2-naphthoyl chloride (210 mg, 1.1 mmol) in $CH_2Cl_2$ (3 ml) was added a solution of aminopyrrolidinone of Example X (300 mg, 1.0 mmol) and triethylamine (0.24 ml, 1.7 mmol) in $CH_2Cl_2$ (3 ml). After stirring for 18 h at room temperature the reaction mixture was evaporated in vacuo to give an oil which was purified by radial chromatography on silica gel eluting with $EtOH/CH_2Cl_2$ (2%) to give the title compound 363 mg (82%).
DSC=124.38°-128.68° C.@49.93 (99.73) J/g.

EXAMPLE 22

Preparation of 1,1-Dimethylethyl cis-4-[[(4-chlorophenyl)carbonyl]amino]-5-oxo-1-pentyl-3-pyrrolidinecarboxylate To a solution of the aminopyrrolidinone of Example T (116 mg, 0.429 mmol) and triethylamine (0.12 ml, 0.858 mmol) in $CH_2Cl_2$ was added a solution of 4-chlorobenzoyl chloride (75 mg, 0.429 mmol) in $CH_2Cl_2$ dropwise via syringe. After stirring for 12 h at room temperature the reaction mixture was evaporated in vacuo to give a residue which was chromatographed on silica gel eluting with $EtOH/CH_2Cl_2$ (2%-5%) to give the title compound (160 mg, 91%) as a colorless solid. DSC=100.4°-105.1° C. at 52.7 J/g. Anal calcd for $C_{21}H_{29}N_2O_4Cl$: C, 61.68; H, 7.15; N, 6.85. Found C, 61.20; H, 7.06; N, 6.58. MS calcd for $C_{21}H_{29}N_2O_4Cl$ 409, found 409.

EXAMPLE 23

Preparation of Ethyl cis-4-[[(4-chlorophenyl)carbonyl]amino]-5-oxo-1-phenyl-3-pyrrolidinecarboxylate To a solution of p-chlorobenzoyl chloride (247 mg, 1.41 mmol) in $CH_2Cl_2$ (4 ml) was added a solution of aminopyrrolidinone of Example S (350 mg, 1.41 mmol) and triethylamine (0.4 ml, 2.82 mmol) in $CH_2Cl_2$ (4 ml) and the resulting solution was stirred for 18 h at room temperature. Concentration in vacuo gave an oil which was chromatographed on silica gel eluting with 5/95 $EtOH/CH_2Cl_2$ to give the title compound (378 mg, 68%) as a solid. Anal calcd for $C_{20}H_{19}N_2O_4Cl$; C, 62.10; H, 4.95; N, 7.24. Found: C, 62.07; H, 5.05; N, 7.18. MS calcd for $C_{20}H_{19}N_2O_4Cl$ 386, found 386. DSC=215.2°-216.8° C. at 144.3 J/g.

EXAMPLE 24

Preparation of ethyl cis-4-[[[(4-chlorophenyl)amino]carbonyl]amino]-5-oxo-1-pentyl-3-pyrrolidinecarboxylate To a solution of 4-chlorophenyl isocyanate (113 mg, 0.734 mmol) in $CH_2Cl_2$ (1 ml) was added the aminopyrrolidinone of Example R (178 mg, 0.734 mmol) in $CH_2Cl_2$ (1 ml). After stirring for 18 h, the solvent was removed in vacuo and the resulting mixture was chromatographed on silica gel (5% $EtOH/CH_2Cl_2$) to give the title compound (210 mg, 72%). 'H NMR (300 MH$_z$, CDCl$_3$) δ7.99 (1H, s), 7.42 (2H, d), 7.24 (2H, t), 6.21 (1H, d), 4.92 (1H, q), 4.21 (1H, m), 4.11 (1H, m), 3.55 (2H, q), 3.32 (2H, m), 1.55 (2H, q), 1.29 (4H, m), 1.21 (2H, t), 0.89 (3H, t).

EXAMPLE 25

Preparation of 1,1-Dimethylethyl cis-4-[(1H-indazol-3-ylcarbonyl)amino]-5-oxo-1-phenyl-3-pyrrolidinecarboxylate To indazole-3-carboxylic acid (176 mg, 1.08 mmol) [prepared according to the procedure in J. Am Chem. Soc. 74, 2009 (1952)] in DMF (2 ml) was added 1,1-carbonyldiimidazole (176 mg, 1.08 mmol). After stirring for 4 h at room temperature a solution of the aminopyrrolidinone of Example V (300 mg, 1.08 mmol) in DMF was added. After stirring for 12 h at room temperature the reaction mixture was evaporated in vacuo to give 260 mg (57%) of an oil which was chromatographed on silica gel eluting with $EtOH/CH_2Cl_2$ (2%-5%) to give the title compound.
Anal calcd for $C_{23}H_{24}N_4O_4$: C, 65.70; H, 5.75; N, 13.32. Found C, 65.73; H, 5.90; N, 13.12. DSC=200.48° C.-205.71° C. at 168.55 J/g.

EXAMPLE 26

Preparation of 1,1-Dimethylethyl cis-5-oxo-1-phenyl-4-[(2-pyrazinylcarbonyl)amino]-3-pyrrolidinecarboxylate To 2-pyrazinecarboxylic acid (90 mg, 0.72 mmol) in DMF (2 ml) was added 1,1-carbonyldiimidazole (117 mg, 0.72 mmol). After stirring for 4 h at room temperature a solution of the aminopyrrolidinone of Example V (200 mg, 0.72 mmol) in DMF was added. After stirring for 18 h at room temperature the reaction mixture was evaporated in vacuo to give an oil which was chromatographed on silica gel eluting with $EtOH/CH_2Cl_2$ (2%-5%) to give the title compound, 140 mg (51%). MS calcd for $C_{20}H_{22}N_4O_4$ 382, found 382.

EXAMPLE 27

Preparation of

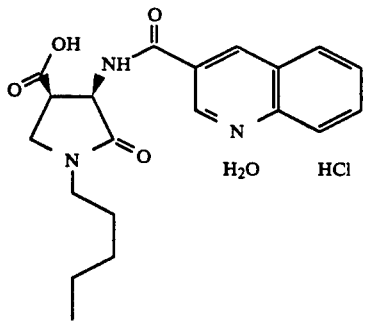

cis-5-oxo-1-pentyl-4-[(3-quinolinylcarbonyl)amino]-3-pyrrolidinecarboxylic acid, monohydrochloride To the ethyl ester of Example 1 (173 mg, 0.435 mmol) dissolved in 4:1 EtOH/THF was added an aqueous solution of lithium hydroxide (31 mg, 1.29 mmol). After stirring for 16 h at room temperature 2.5 ml of water was added and the solution was extracted with chloroform. The aqueous layer was then acidified with 1N HCl to pH=2 and extracted again with chloroform. The combined organic layers were dried over MgO$_4$, filtered and concentrated in vacuo to give the crude acid which was chromatographed on silica gel eluting with 5/95/1 EtOH/CH$_2$Cl$_2$/HOAc to give the title compound (31 mg, 19%) as a colorless powder. MS M+1 calcd for C$_{20}$H$_{23}$N$_3$O$_4$ 370; found 370.

EXAMPLE 28

Preparation of

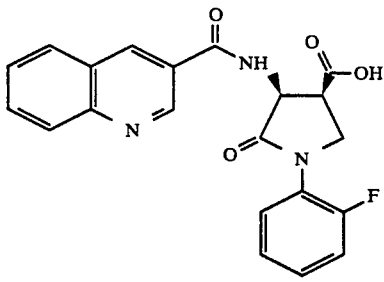

cis-1-(2-fluorophenyl)-5-oxo-4-[(3-quinolinylcarbonyl)amino]5-oxo-3-pyrrolidinecarboxylic acid The tert-butyl ester of Example 3 (223 mg, 0.496 mmol) was dissolved in trifluoroacetic acid (11 ml) and stirred for 8 h at room temperature. Concentration in vacuo gave a yellow oil which was purified by radial chromatography on a silica gel plate (2 mm) eluting with 10/89/1 EtOH/CH$_2$Cl$_2$/HOAc to give the title compound (178 mg, 63%). MS calcd for C$_{21}$H$_{16}$N$_3$O$_4$F 393, found 393. DSC=293.2°-297.4° C. @147.7 J/g.

EXAMPLE 29

Preparation of

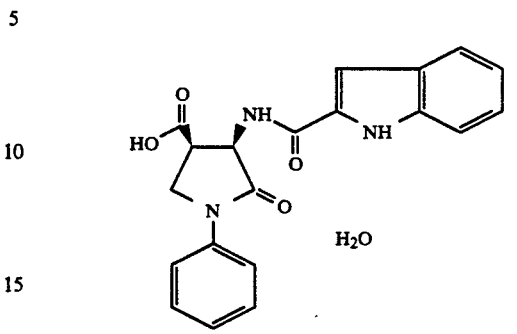

cis-4-[(1H-indol-2-ylcarbonyl)amino]-5-oxo-1-phenyl-3-pyrrolidinecarboxylic acid The tert-butyl ester of Example 5 (110 mg, 0.26 mmol) was dissolved in 3 ml of trifluoroacetic acid and the resulting solution was stirred for 2 days at room temperature. Concentration in vacuo gave an oil which was chromatographed on silica gel eluting with 5/91/1 EtOH/CH$_2$Cl$_2$/HOAc to give the title compound (41 mg, 43%) as a colorless solid. MS calcd C$_{20}$H$_{17}$N$_3$O$_4$ 363, found 363. DSC=214.2°-229.3° C. @48.7 J/g.

EXAMPLE 30

Preparation of

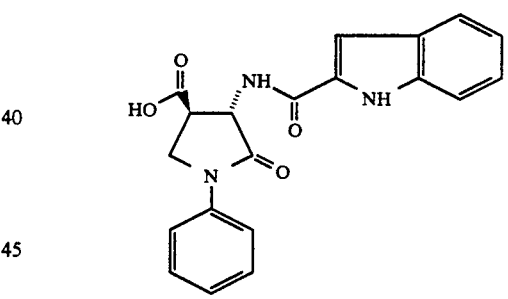

trans-4-[(1H-Indol-2-ylcarbonyl)amino]-5-oxo-1-phenyl-3-pyrrolidinecarboxylic acid To the ethyl ester of Example 4 (68 mg, 0.174 mmol) dissolved in 4:1 EtOH/THF was added an aqueous solution of lithium hydroxide (13 mg, 0.521 mmol). After stirring for 16 h at room temperature, 2.5 ml of water was added and the solution was extracted with chloroform. The aqueous layer was then acidified with 1N HCl to pH2 and extracted again with chloroform. The combined organic layers were dried over MgO$_4$, filtered and concentrated in vacuo to give the crude acid which was chromatographed on silica gel eluting with 5/95/1 EtOH/CH$_2$Cl$_2$/HOAc to give the title compound (27 mg, 42%) as a colorless powder. Anal calcd for C$_{20}$H$_{17}$N$_3$O$_4$: C, 64.51; H, 4.87; N, 11.28. Found: C, 64.26; H, 4.62; N, 10.88. MS M+1 calcd for C$_{20}$H$_{17}$N$_3$O$_4$ 364, found 364.

EXAMPLE 31

Preparation of

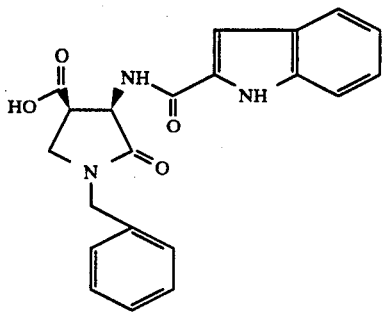

cis-4-[(1H-indol-2-ylcarbonyl)amino]-5-oxo-1-(phenyl-methyl)-3-pyrrolidinecarboxylic acid The tert-butyl ester 320 mg (0.738 mmol) of Example 6 was dissolved in trifluoroacetic acid (2 ml) and stirred for 3.5 h at room temperature after which time the reaction was concentrated in vacuo. The resulting material was recrystallized from $CH_2Cl_2$, to give 94 mg (34%) of the title compound. Anal calcd for $C_{21}H_{19}N_3O_4 \cdot \frac{1}{4}H_2O$.C,66.04; H,5.15; N,11.00. Found C,66.21; H,5.34; N,10.62. MS calcd 377, found 377. DSC=240.75°–246.18° C. @122.6 J/g.

EXAMPLE 32

Preparation of

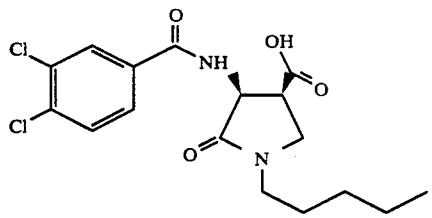

cis-4-[[(3,4-Dichlorophenyl)carbonyl]amino]-5-oxo-1-pentyl-3-pyrrolidinecarboxylic acid The tert-butyl ester of Example 9 (145 mg, 0.327 mmol) was dissolved in 5 ml of trifluoroacetic acid and stirred for 16 h at room temperature after which time the reaction was concentrated in vacuo. The resulting material was radially chromatographed on silica gel eluting with $EtOH/CH_2Cl_2/HOAc$ (5/95/1) to give the title compound (89 mg, 77%) as a colorless solid. Anal calcd for $C_{17}H_{20}N_2O_4Cl_2$: C, 52.73; H, 5.20; N, 7.23. Found: C, 52.43; H, 5.32; N, 7.02. DSC=204.6°–210.2° C.@54.8 J/g. MS M+1 calcd for $C_{17}H_{20}N_2O_4Cl_2$ 387, found 387.

EXAMPLE 33

Preparation of

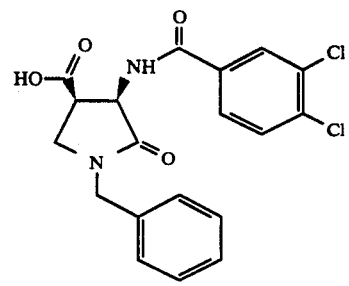

cis-4-[[(3,4-dichlorophenyl)carbonyl]amino]-5-oxo-1-(phenylmethyl)-3-pyrrolidinecarboxylic acid The tert-butyl ester of Example 14 (301 mg, 0.65 mmol) was dissolved in trifluoroacetic acid (3 ml) and stirred for 3.5 h after which time the reaction was concentrated in vacuo. The residue was suspended in $CH_2Cl_2$ and filtered to give 155 mg (58%) of the title compound as a solid. Anal Calcd for $C_{19}H_{16}N_2O_4Cl_2 \cdot \frac{1}{4} H_2O$: C,55.42; H,4.04; N,6.80. Found: C.55.43; H,4.13; N,6.83. DSC=217.26°–219.87° C. at 104.8 J/g. MS M+1 calcd for $C_{19}H_{16}N_2O_4Cl_2$ 408, found 408.

EXAMPLE 34

Preparation of

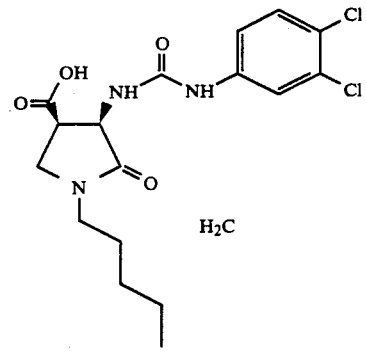

cis-4-[[[(3,4-dichlorophenyl)amino]carbonyl]amino]-5-oxo-1-pentyl-3-pyrrolidinecarboxylic acid The tert-butyl ester of Example 10 (160 mg, 0.35 mmol) was dissolved in 5ml of trifluoroacetic acid and stirred for 16 h at room temperature after which time the reaction was concentrated in vacuo. The resulting material was radially chromatographed on silica gel eluting with $EtOH/CH_2Cl_2/HOAc$ (5/95/1) to give the title compound (119 mg, 85%) as a colorless solid. DSC=139.0°–143° C. @5.7 J/g and 191.7°– 203.5° C.@99.6 J/g. MS M+1 calcd for $C_{17}H_{21}N_3O_4Cl_2$ 403, found 403.

EXAMPLE 35

Preparation of

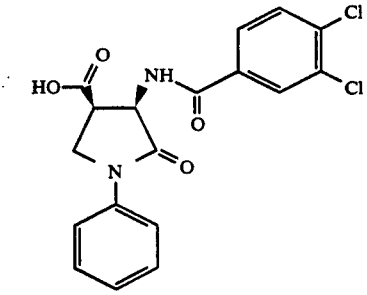

cis-4-[[(3,4-dichlorophenyl)carbonyl]amino]-5-oxo-1-phenyl-3-pyrrolidinecarboxylic acid (Compound A) and

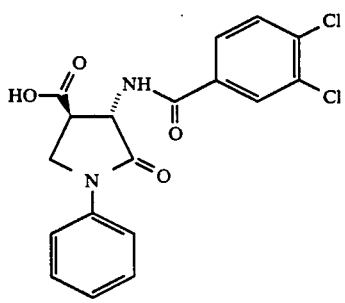

trans-4-[[(3,4-dichlorophenyl)carbonyl]amino]-5-oxo-1-phenyl-3-pyrrolidinecarboxylic acid (Compound B)

To a solution of ethyl ester of Example 11 (394 mg, 0.935 mmol) in EtOH/THF (10 ml, 4:1 EtOH/THF) was added a solution of lithium hydroxide (33 mg, 1.4 mmol) in 1 ml H$_2$O and the resulting solution was stirred for 2 h at room temperature. Concentration in vacuo gave a solid which was chromatographed on silica gel eluting with 2/97/1 EtOH/CH$_2$Cl$_2$/HOAc to give the cis-substituted carboxylic acid Compound A (31 mg, 8.4%) as a colorless solid. Anal calcd for C$_{18}$H$_{14}$N$_2$O$_4$Cl$_2$: C, 54.97; H, 3.59; N, 7.12. Found: C, 55.10; H, 3.61; N, 6.66. MS M+1 calcd for C$_{18}$H$_{14}$N$_2$O$_4$Cl$_2$ 394, found 394. DSC=220°-227.7° C. at 70.9 J/g. Continued elution gave the trans-substituted carboxylic acid Compound B (290 mg, 79%) as a colorless solid. Anal calcd for C$_{18}$H$_{14}$N$_2$O$_4$Cl$_2$: C, 54.97; H, 3.59; N, 7.12. Found: C, 54.70; H, 3.51; N, 6.98. MS M+1 calcd for C$_{18}$H$_{14}$N$_2$O$_4$Cl$_2$ 394, found 394. DSC=234.2°-237.0° C.@80.1 J/g.

EXAMPLE 36

Preparation of

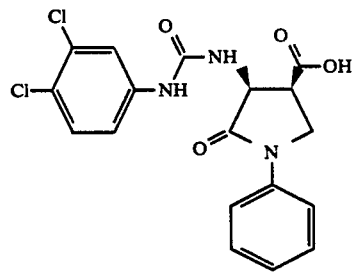

cis-4-[[[(3,4-dichlorophenyl)amino]carbonyl]amino]-5-oxo-1-phenyl-3-pyrrolidinecarboxylic acid (Compound A) and

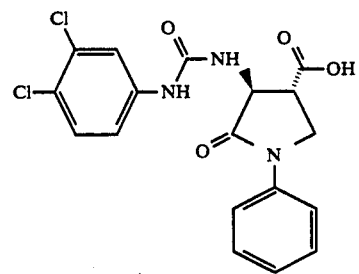

trans-4-[[[(3,4-dichlorophenyl)amino]carbonyl]amino-5-oxo-1-phenyl-3-pyrrolidinecarboxylic acid (Compound B)

To a solution of ethyl ester of Example 12 (420 mg, 0.96 mmol) in EtOH/THF (10 ml of 1:4 EtOH/THF) was added a solution of lithium hydroxide (35 mg, 1.4 mmol) in H$_2$O (3 ml) and the resulting solution was stirred for 2 h at room temperature. The reaction mixture was then acidified to pH=2 with 1N HCl. Removal of the solvent gave a yellow solid which was chromatographed on silica gel eluting with 2/97/1 EtOH/CH$_2$Cl$_2$/HOAc to give the cis-substituted Compound A (62 mg, 16%) as a colorless solid. MS calcd for C$_{18}$H$_{15}$N$_3$O$_4$Cl$_2$ 408, found 408. DSC=229.1°-238.7° C.@281.6 J/g. Continued elution gave the trans-substituted Compound B (160 mg, 41%) as a colorless solid: MS calcd for C$_{18}$H$_{15}$N$_3$O$_4$Cl$_2$ 408, found 408. DSC=243.5°-249.7° C.@218.2 J/g.

EXAMPLE 37

Preparation of

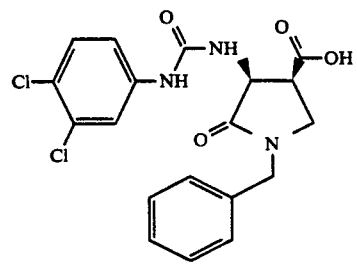

Cis-4-[[[(3,4-dichlorophenyl)amino]carbonyl]amino-5-oxo-1-phenylmethyl-3-pyrrolidinecarboxylic acid The tert-butyl ester of Example 15 (410 mg, 0.857 mmol) was dissolved in trifluoroacetic acid (3 ml) and stirred for 4 h after which time the reaction was concentrated in vacuo. The residue was resuspended in MeOH and filtered to give the title compound (143 mg, 40%) as a solid. Anal calcd for $C_{19}H_{17}N_3O_4Cl_2 \cdot \frac{1}{4}H_2O$: C,53.47; H,4.13; N,9.85. Found C,53.24; H,4.12; N,9.63. DSC=213.82°–216.88° C. @121.3 J/g.

EXAMPLE 38

Preparation of

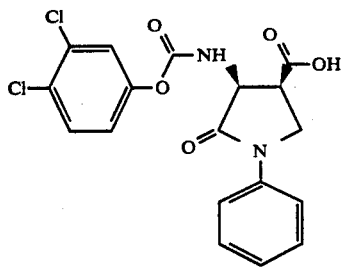

cis-4-[[(3,4-Dichlorophenoxy)carbonyl]amino]-5-oxo-1-phenyl-3-pyrrolidinecarboxylic acid The tert-butyl ester of Example 13 is dissolved in trifluoroacetic acid and stirred for 16 h at room temperature after which time the reaction is concentrated in vacuo. The resulting material is purified by chromatography on silica gel eluting with EtOH/CH₂Cl₂/HOAc to give the title compound.

EXAMPLE 39

Preparation of

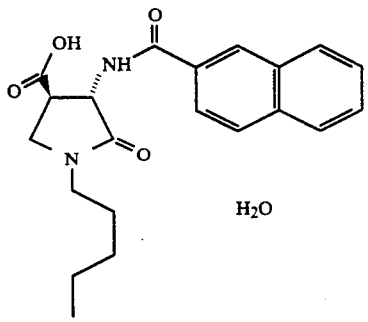

trans-4-[(2-Naphthalenylcarbonyl)amino]-5-oxo-1-pentyl-3-pyrrolidinecarboxylic acid To the ethyl ester of Example 16 (170 mg, 0.429 mmol) dissolved in 4:1 EtOH/THF was added an aqueous solution of lithium hydroxide (31 mg, 1.29 mmol). After stirring for 16 h at room temperature, 2.5 ml of water was added and the solution was extracted with chloroform. The aqueous layer was then acidified with 1N HCl to pH=2 and extracted again with chloroform. The combined organic layers were dried over MgO₄, filtered and concentrated in vacuo to give the crude acid which was chromatographed on silica gel eluting with 5/95/1 EtOH/CH₂Cl₂/HOAc to give the title compound (45 mg, 28%) as a colorless powder. Anal calcd for $C_{21}H_{26}N_2O_5 \cdot H_2O$: C, 65.27; H, 6.26; N, 7.61. Found C, 65.45; H, 6.52; N, 7.11. MS M+1 calcd for $C_{21}H_{26}N_2O_5$ 369, found 369.

EXAMPLE 40

Preparation of

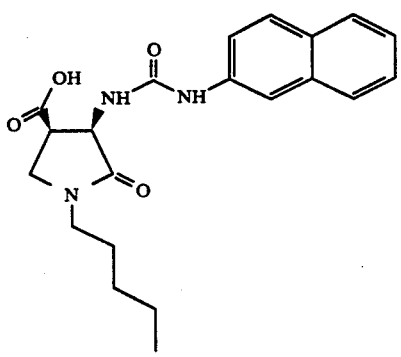

cis-4-[[(2-Naphthalenylamino)carbonyl]amino]-5-oxo-1-pentyl-3-pyrrolidinecarboxylic acid The tert-butyl ester of Example 17 (130 mg, 0.296 mmol) was dissolved in 5 ml of trifluoroacetic acid and stirred for 16 h at room temperature after which time the reaction was concentrated in vacuo. The resulting material was chromatographed on silica gel on a chromatotron plate eluting with EtOH/CH₂Cl₂/HOAc (5/95/1) to give the title compound (63 mg, 55%) as a colorless solid. Anal calcd. for $C_{21}H_{25}N_3O_5$: C, 65.78; H, 6.57; N, 10.96. Found: C, 65.31; H, 6.62; N, 10.75. DSC=228.8°–231.3 at 293.2 J/g. MS calcd for $C_{21}H_{25}N_3O_5$ 383, found 383.

EXAMPLE 41

Preparation of

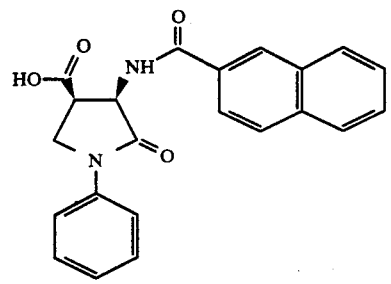

cis-4-[(2-Naphthalenylcarbonyl)amino]-5-oxo-1-phenyl-3-pyrrolidinecarboxylic acid (Compound A) and

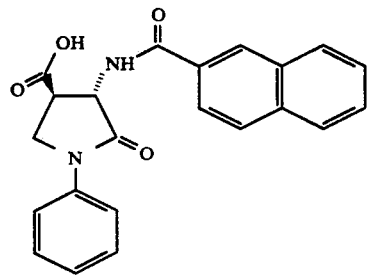

trans-4-[(2-Naphthalenylcarbonyl)amino]-5-oxo-1-phenyl-3-pyrrolidinecarboxylic acid (Compound B)

To the ethyl ester of Example 18 (1.92 g, 4.8 mmol) dissolved in 4:1 EtOH/THF (100 ml) was added a solution of lithium hydroxide (575 mg, 24 mmol). After stirring for 2 h at room temperature, 70 ml of water was added and the solution was extracted with chloroform. The aqueous layer was then acidified with 1N HCl to pH=2 and extracted again with chloroform. The combined organic layers were dried over MgO$_4$, filtered and concentrated in vacuo to give the crude acid which was recrystallized from CH$_2$Cl$_2$ to give the trans carboxylic acid Compound B (1.19 g, 66%) as a colorless powder. Anal calcd for C$_{22}$H$_{18}$N$_2$O$_4$.$\frac{1}{2}$H$_2$O: C, 68.92; H, 4.99; N, 7.30. Found: C, 68.57; H, 4.68; N, 7.17. MS M+1 calcd for C$_{22}$H$_{18}$N$_2$O$_4$ 375; found 375. DSC=250.0°-251.9 at 112.3 J/g. Chromatography of the mother liquor on silica gel eluting with 10/89/1 EtOH/CH$_2$Cl$_2$/HOAc gave the higher-Rf, cis isomer Compound A (232 mg, 12%) as a colorless powder. Anal calcd for C$_{22}$H$_{18}$N$_2$O$_4$.$\frac{1}{4}$H$_2$O: C, 69.74; H, 4.92; N, 7.39. Found: C, 69.90; H, 4.94; N, 7.19. DSC=211.7°-214.9° C. at 94.5 J/g. MS calcd for C$_{22}$H$_{18}$N$_2$O$_4$ 374, found 374.

EXAMPLE 42

Preparation of

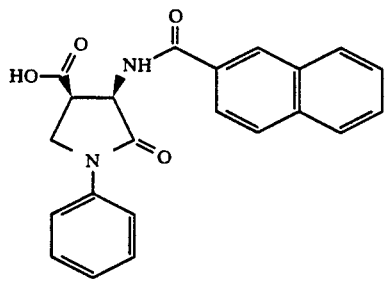

cis-4-[(2-Naphthalenylcarbonyl)amino]-5-oxo-1-phenyl-3-pyrrolidinecarboxylic acid The tert-butyl ester of Example 19 (2.14 g, 7.97 mmol) was dissolved in 10 ml of trifluoroacetic acid and stirred for 18 h at room temperature after which time the reaction was concentrated in vacuo. The resulting solid was purified by chromatography on silica gel eluting with EtOH/CH$_2$Cl$_2$/HOAc (3/96/1) to give the title compound (1.56 g, 84%) as a colorless solid. Anal calcd. for C$_{22}$H$_{18}$N$_2$O$_4$.$\frac{1}{4}$H$_2$O: C, 69.74; H, 4.92; N, 7.39. Found: C, 69.90; H, 4.86; N, 7.30. MS calcd for C$_{22}$H$_{18}$N$_2$O$_4$ 374, found 374. DSC=212.9°-216.0° C. at 100.9 J/g.

EXAMPLE 43

Preparation of

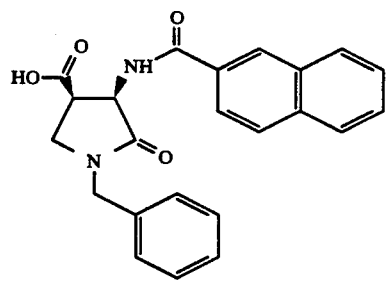

cis-4-[(2-Naphthalenylcarbonyl)amino]-5-oxo-1-(phenylmethyl)-3-pyrrolidinecarboxylic acid The tert-butyl ester of Example 21 (303 mg, 0.7 mmol) was dissolved in trifluoroacetic acid (3 ml) and stirred for 3.5 h after which time the reaction was concentrated in vacuo. Resuspension of the residue in CH$_2$Cl$_2$ and filtration gave the title compound (161 mg, 59%) as a solid. Anal calcd for C$_{23}$H$_{20}$N$_2$O$_4$.$\frac{1}{4}$H$_2$O: C, 70.30; H,5.26; N,7.13. Found C,70.52; H,5.44; N,7.10. DSC=213.37°-216.45° C. @107.5 J/g. MS calc for C$_{23}$H$_{20}$N$_2$O$_4$ 388, found 388.

EXAMPLE 44

Preparation of

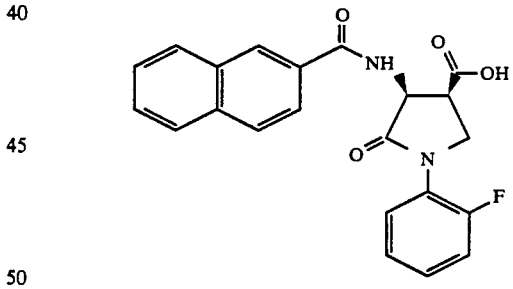

cis-1-(2-Fluorophenyl)-4-[(2-naphthalenylcarbonyl)amino]-5-oxo-3-pyrrolidinecarboxylic acid The tert-butyl ester of Example 20 (388 mg, 0.865 mmol) was dissolved in 3 ml of trifluoroacetic acid and stirred for 18 h at room temperature. Concentration in vacuo gave a solid which was chromatographed on a silica gel chromatotron plate (4 mm) eluting with 3/1/96 EtOH/CH$_2$Cl$_2$/HOAc to give the title compound (183 mg, 54%) as a solid. Anal calcd for C$_{22}$H$_{17}$N$_2$O$_4$F. H$_2$O: C, 66.40; H, 4.67; N, 6.83. Found C, 64.55; H, 4.42; N, 6.71. MS calcd for C$_{22}$H$_{17}$N$_2$O$_4$F 392, found 392. DSC=182.9°-185.2° C.@94.1 J/g.

EXAMPLE 45

Preparation of

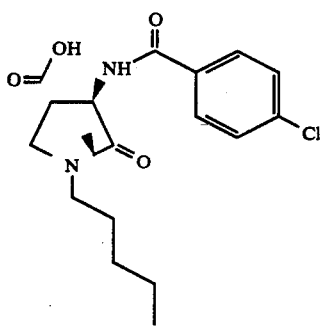

cis-1-[[(4-Chlorophenyl)carbonyl]amino]-5-oxo-1-pentyl-3-pyrrolidinecarboxylic acid The tert-butyl ester of Example 22 (160 mg, 0.39 mmol) was dissolved in 4 ml of trifluoroacetic acid and stirred for 16 h at room temperature after which time the reaction was concentrated in vacuo. The resulting material was chromatographed on silica gel on a chromatotron plate eluting with EtOH/CH$_2$Cl$_2$/HOAc (5/95/1) to give the title compound (65 mg, 41%) as a colorless solid. DSC=193.3°–195.8° C.@71.2 J/g.

MS calcd for C$_{17}$H$_{21}$N$_2$O$_4$Cl 352, found 352.

EXAMPLE 46

Preparation of

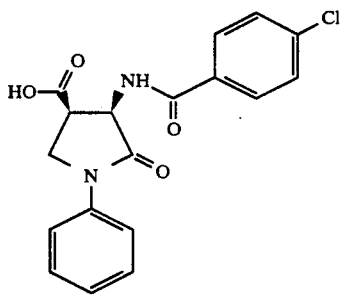

cis-4-[[(4-Chlorophenyl)carbonyl]amino]-5-oxo-1-phenyl-3-pyrrolidinecarboxylic acid (Compound A) and

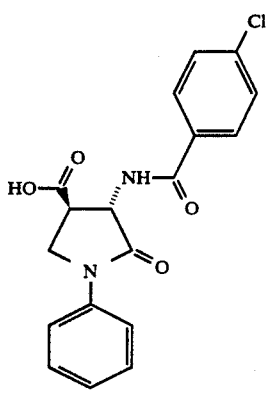

trans-4-[[(4-Chlorophenyl)carbonyl]amino]-5-oxo-1-phenyl-3-pyrrolidinecarboxylic acid (Compound B)

To a solution of ethyl ester of Example 23 (378 mg, 0.977 mmol) in EtOH/THF (10 ml of 1:4 EtOH THF) was added a solution of lithium hydroxide (35 mg, 0.147 mmol) in H$_2$O (1 ml) and the resulting solution was stirred for 2 h at room temperature. Concentration in vacuo gave a residue which was chromatographed on silica gel eluting with 2/97/1 EtOH/CH$_2$Cl$_2$/HOAc to give the desired cis-substituted Compound A (28 mg, 8%) as a colorless solid. MS M+1 calcd for C$_{18}$H$_{14}$N$_2$O$_4$Cl 359, found 359. DSC=211.71°–220.08@51.42 J/g. Continued elution afforded the trans-substituted carboxylic acid Compound B (213 mg, 61%) as a colorless solid. Anal calcd for C$_{18}$H$_{14}$N$_2$O$_4$Cl.½H$_2$O: C, 58.79; H, 4.38; N, 7.61. Found: C, 58.41; H, 4.35; N, 7.10. MS calcd for C$_{18}$H$_{14}$N$_2$O$_4$Cl 358, found 358. DSC=216.2°–223.0° C.@84.2 J/g.

EXAMPLE 47

Preparation of

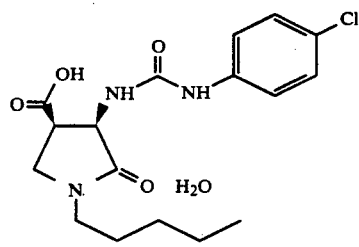

cis-4-[[[(4-chlorophenyl)amino]carbonyl]amino]-5-oxo-1-pentyl-3-pyrrolidinecarboxylic acid and

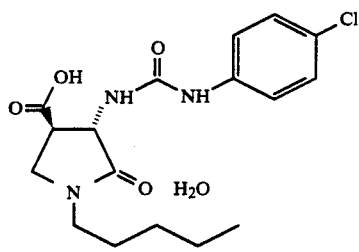

trans-4-[[[(4-chlorophenyl)amino]carbonyl]amino]-5-oxo-1-pentyl-3-pyrrolidinecarboxylic acid To a solution of the ethyl ester (210 mg, 0.530 mmol) of example 24 in 1:4 EtOH/THF (4 ml) was added a solution of lithium hydroxide (13 mg, 0.53 mmol) in water (1 ml) and the reaction was stirred at room temperature for 2 h. The reaction mixture was acidified with 1N HCl to pH=4 and concentrated in vacuo to give a solid which was purified by chromatography on silica gel eluting with MeOH/CH$_2$Cl$_2$/HOAc (10/89/1) to give the cis isomer (70. mg, 38%): Anal calcd for C$_{17}$H$_{22}$N$_3$O$_4$Cl.H$_2$O: C, 52.92; H, 5.75; N, 10.89. Found: C, 52.97; H, 5.64; N, 10.36. MS calcd for C$_{17}$H$_{22}$N$_3$O$_4$Cl 368, found 368. Continued elution gave the trans isomer (88 mg, 45%).

Anal calcd for $C_{17}H_{22}N_3O_4Cl\cdot H_2O$: C, 52.92; H, 5.75; N, 10.89. Found: 53.17; H, 5.79; N, 10.40. MS Calcd for $C_{17}H_{22}N_3O_4Cl$ 368, found 368.

EXAMPLE 48

Preparation of

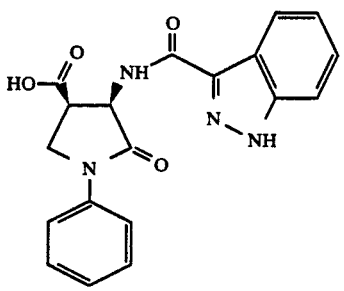

cis-4-[(1H-Indol-3-ylcarbonyl)amino]-5-oxo-1-phenyl-3-pyrrolidinecarboxylic acid The tert-butyl ester (230 mg, 0.547 mmol) of Example 25 was dissolved in trifluoroacetic acid (3 ml) and stirred for 20 min at room temperature after which time the reaction was concentrated in vacuo. Resuspension of the residue in $CH_2Cl_2$ and filtration gave the title compound (206 mg, 79%) as a colorless solid. Anal calcd for $C_{19}H_{16}N_4O_4\cdot 8/10CF_3CO_2H$: C,54.41; H,3.55; N,12.32; F,10.03. Found C,54.52; H,3.76; N,12.45; F,10.35. DSC=130.85°–140.96° C. at 97.64 J/g. MS calc. for $C_{19}H_{16}N_4O_4$ 364, found 364.

EXAMPLE 49

Preparation of

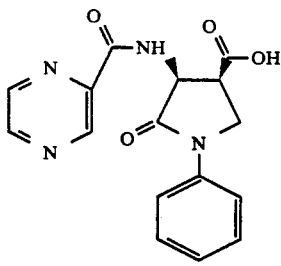

cis-5-Oxo-1-phenyl-4-[(2-pyrazinylcarbonyl)amino]-3-pyrrolidinecarboxylic acid

The tert-butyl ester of (120 mg 0.314 mmol) of Example 26 was dissolved in trifluoroacetic acid 2 ml and stirred for 3.5 h at room temperature after which time the reaction was concentrated in vacuo. The resulting material was chromatographed on silica gel eluting with $EtOH/CH_2Cl_2/HOAc$ (5/95/1) to give 55 mg (54%) of the title compound, MS calcd for $C_{16}H_{14}N_4O_4$: 316, found 326.

EXAMPLE 50

Preparation of

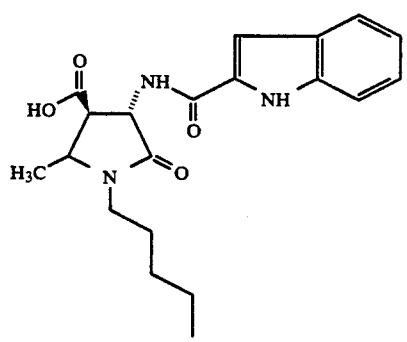

4-[(1H-Indol-2-ylcarbonyl)amino]-2-methyl-5-oxo-1-pentyl-3-pyrrolidinecarboxylic acid To a solution of Example 7 (600 mg, 1.5 mmol) in EtOH/THF (20 ml of 1:4 EtOH/THF) was added a solution of lithium hydroxide (55 mg, 2.3 mmol) in $H_2O$ (10 ml) and the resulting solution was stirred for 2 h at room temperature. The reaction mixture was then acidified to pH 2 with 1N HCl. Removal of the solvent gave the title compound.

EXAMPLE 51

Preparation of

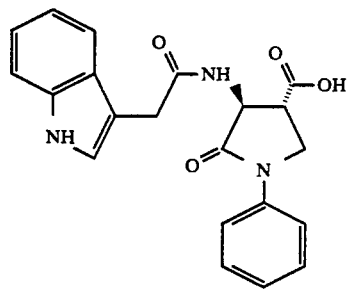

trans-4-[(3-indolylacetyl)amino]-5-oxo-1-phenyl-3-pyrrolidinecarboxylic acid

To the title compound of example 8 (520 mg, 1.28 mmol) in 1:4 THF/EtOH (20 ml) was added lithium hydroxide (46 mg (1.92 mmol) in $H_2O$ (10 ml) and stirred for 2.5 h. The reaction mixture was acidified with 1N HCl to pH 3 and concentrated in vacuo. The mixture was purified by chromatography on silica gel ($CH_3OH/HOAc/CH_2Cl_2$ gradient 10/1/89 to 20/1/79) to give 124 mg (18%) of the title compound. MS calcd for $C_{21}H_{19}N_3O_4$: 377, found 377.

EXAMPLE 52

Preparation of
cis-4-[(2-Naphthalenylcarbonyl)amino]-5-oxo-1-phenyl-3-pyrrolidinecarboxamide The product of example 42 is treated with oxalyl chloride and a catalytic amount of DMF in $CH_2Cl_2$. After 2 h at room temperature the solution is concentrated in vacuo. The acid chloride is then redissolved in $CH_2Cl_2$ and treated with gaseous ammonia. An aqueous workup and purification via chromatography affords the title compound.

EXAMPLE 53

Preparation of

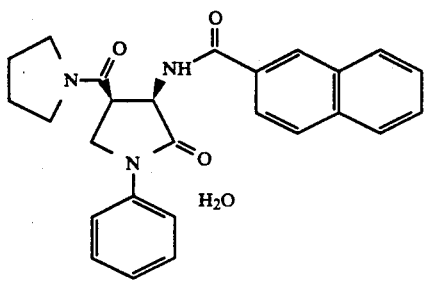

·H₂O cis-1-[[3-[(2-Naphthalenylcarbonyl)amino]-2-oxo-1-phenyl-4-pyrrolidinyl]carbonyl]pyrrolidine To the product of Example 42 (100 mg, 0.264 mmol) in DMF (2.5 ml) was added 1,1-carbonyldiimidazole (43 mg, 0.264 mmol). After stirring for 3 h at room temperature, pyrrolidinone (19 mg, 0.264 mmol) was added and the reaction was then stirred for 18 h at room temperature. After removal of the solvent in vacuo, a solution of $K_2CO_3$ (36 mg) in $H_2O$ (5 ml) was added and the mixture was extracted with $CH_2Cl_2$. The $CH_2Cl_2$ extractions were washed with $H_2O$ and brine and then dried ($MgO_4$) and concentrated to give an oil which was chromatographed on a silica gel chromatotron plate (2 mm) eluting with 5% $EtOH/CH_2Cl_2$ to give the diamide title compound (32 mg, 28%). Anal calcd for $C_{26}H_{24}N_3O_3·H_2O$: C, 70.10; H, 6.11; N, 9.43. Found: C, 70.27; H, 5.77; N, 9.24. MS calcd for $C_{26}H_{24}N_3O_3$ 427, found 427. DSC=208.6°–209.8° C.@96 J/g.

EXAMPLE 54

Preparation of

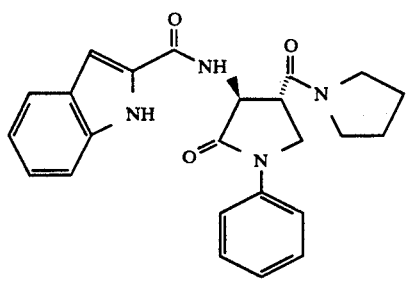

trans-N-[2-oxo-1-phenyl-4-(1-pyrrolidinylcarbonyl)-3-pyrrolidinyl]-1H-indole-2-carboxamide To a solution of the product of example 20 (103 mg, 0.283 mmol) in DMF (2 ml) was added 1,1-carbonyl-diimidazole (46 mg, 0.283 mmol). After stirring for 5.5 h, pyrrolidine (0.05 ml, 0.566 mmol) was added and the reaction was stirred for 18 h. The resulting precipitate was filtered and then worked with $CH_3OH$ to give 91 mg (77%) of the title compound. MS calcd for $C_{24}H_{24}N_4O_4$: 416, found 416. DSC=218.72°–234.43° C.

EXAMPLE 55

Preparation of

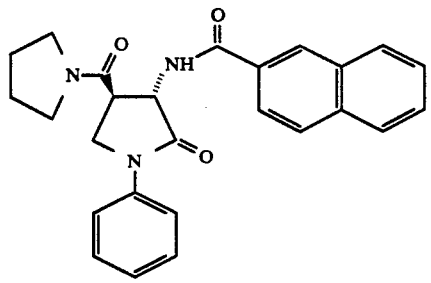

trans-1-[[3-[(2-Naphthalenylcarbonyl)amino]-2-oxo-1-phenyl-4-pyrrolidinyl]carbonyl]pyrrolidine To a solution of the product of Example 41 (Compound B) (106 mg, 0.28 mmol) in DMF (2 ml) was added 1,1-carbonyldiimidazole (45 mg, 0.28 mmol). After stirring for 5 h, pyrrolidine (0.23 ml, 2.8 mmol) was added and the reaction was stirred for 48 h at room temperature. Evaporation of the solvent in vacuo gave a yellow oil which was purified by radial chromatography (silica gel, 2 mm plate) eluting with 3% $EtOH/CH_2Cl_2$ to give the title diamide compound (80 mg, 67%). Anal calcd for $C_{26}H_{24}N_3O_3·\frac{1}{2}H_2O$: C, 71.54; H, 6.00; N, 9.62. Found: C, 71.38; H, 6.08; N, 9.31. MS calcd for $C_{26}H_{24}N_3O_3$ 427, found 427. DSC=206.8°–208.1° C.@79.9 J/g.

EXAMPLE 56

Preparation of trans-4 [(2-Naphthalenylcarbonyl)amino]-5-oxo-1-phenyl-3-pyrrolidine carboxamide The trans-product of example 41 is converted to the corresponding primary amide via the acid chloride as described for example 52.

EXAMPLE 57

Preparation of

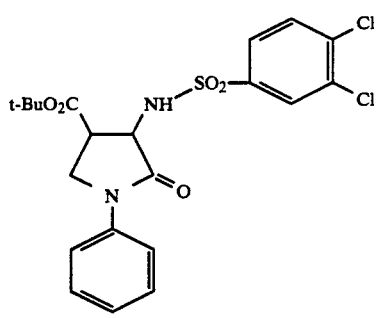

1,1-Dimethylethyl cis-4-[[(3,4-dichlorophenyl)sulfonyl]amino]-5-oxo-1-phenyl-3-pyrrolidinecarboxylic acid To a solution of the aminopyrrolidinone (150 mg, 5.43 mmol) of Example V and triethylamine (0.15 ml, 10.9 mmol) in $CH_2Cl_2$ (2 ml) was added 3,4-dichlorophenylsulfonyl chloride (133 mg) 5.43 mmol). The reaction was then stirred for 18 h at room temperature after which time the solvent was evaporated. The residue was chromatographed on silica gel eluting with EtOH/CH₂H₂(3/97) to give the desired title sulfonamide, 180 mg (73%). Anal. calcd. for C₂₁H₂₂N₂O₅Cl₂S: C,51.97; H,4.57; N,5.77. Found C,51.50; H,4.61; N,5.58. MS calcd. for: C₂₁H₂₂N₂O₅Cl₂S 585, Found 484.

EXAMPLE 58

Preparation of 1,1-dimethylethyl cis-4-[(2-naphthalenylsulfonyl)amino]-5-oxo-1-phenyl-3-pyrrolidinecarboxylate

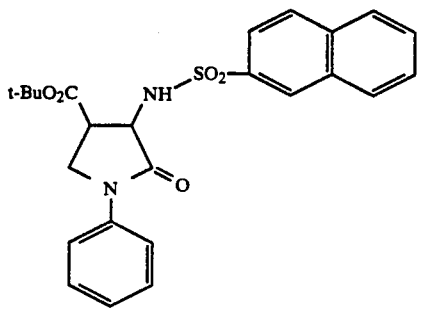

To a solution of 2-naphthalene sulfonylchloride (0.238 mg, 1.05 mmol) in CH₂Cl₂ (2 ml) was added a solution of the aminopyrrolidinone of Example V (0.290 mg, 1.05 mmol) and triethylamine (0.15 ml, 1.05 mmol) in CH₂Cl₂ (3 ml) and stirred for 18 h. The desired solid was then filtered. The filtrate was purified by radial chromatography (2% EtOH/CH₂H₂) to give additional desired material. Recrystallization of the combined solids from CH₂Cl₂ afforded the title compound (375 mg, 80%). Anal. calcd. for C₂₅H₂₆N₂O₅S.½H₂O: C, 63.54; H, 5.69; N, 5.93. Found: C, 63.86; H, 5.69; N, 5.71. DSC=192.01°-194.52° C. at 73.88 J/g.

EXAMPLE 59

Preparation of

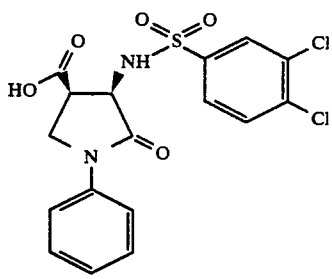

cis-4-[[3,4-Dichlorophenyl)sulfonyl]amino]-5-oxo-1-phenyl-3-pyrrolidinecarboxylic acid The title compound of Example 57 (140 mg, 0.288 mmol) was dissolved in trifluoroacetic acid (2 ml) and stirred for 3.5 h at room temperature after which time the reaction was concentrated in vacuo. Resuspension of the residue in CH₂Cl₂ and filtration gave 84 mg (68%) of the title compound as a solid. Anal. calcd. for C₁₇H₁₄N₂SO₅Cl₂: C, 47.57; H, 3.29; N, 6.53. Found: C, 47.26; H, 3.25; N, 6.49. MS calcd. for C₁₇H₁₄N₂SO₅Cl₂ 430, found 430. DSC=168.46° C. at 32.01 J/g and 174.86° C. at 30.17 J/g.

EXAMPLE 60

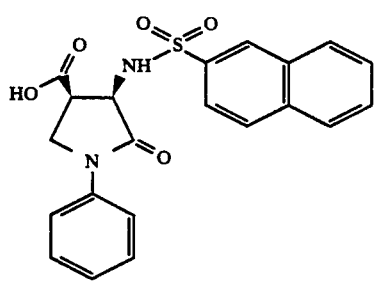

cis-4-[(2-Naphthalenylsulfonyl)amino]-5-oxo-1-phenyl-3-pyrrolidinecarboxylic acid The tert-butyl ester of example 58 (320 mg, 0.686 mmol) was dissolved trifluoroacetic acid (2 ml) and stirred for 2.5 h after which time the reaction was concentrated in vacuo. The resulting material was recrystallized from CH₂Cl₂/CH₃OH to give 116 mg (41%) of the title compound as a white solid. Anal. calcd. for C₂₁H₁₈N₂O₅S.½H₂O: C,60.79; H,4.49; N,6.75. Found: C,60.94; H,4.45; N,6.71. MS calc for C₂₁H₁₈N₂O₅S 410, found 410. DSC=221.0°-224.1° C. at 109.2 J/g.

EXAMPLE 61

Preparation of 1-Phenyl-2,3-pyrrolidinedione

According to the procedure of Southwick [J. Org. Chem. 21, 1087 (1956)] the ethyl ester pyrrolidinone of Example S (1.0 g, 4.0 mmol) was suspended in 75 ml of 20% HCl/H₂O and refluxed for 3.5 h The reaction was cooled and filtered and the filtrate was extracted with CHCl₃ (4×150 ml). Concentration of the combined extracts gave an off-white solid (358 mg). 'NMR(300 MHZ, CDCl₃) δ2.92 (t, 2H), 4.17 (t, 2H), 7.32 (t, 1H), 7.98 (t, 2H), 7.84 (d, 2H).

EXAMPLE 62

Preparation of Ethyl 4,5-dioxo-1-phenyl-3-pyrrolidineacetate

A solution of the product of Example 61 in THF is added to a solution of lithium di-iso-propylamide (LDA) in THF at −78° C. After 2 h at −78° C. a solution of ethyl bromoacetate is added and the reaction is allowed to warm to room temperature. After an aqueous workup the crude product is chromatographed on silica gel to give the title compound.

EXAMPLE 63

Preparation of Ethyl 4-(hydroxyimino)-5-oxo-1-phenyl-3-pyrrolidineacetate

A solution of product of Example 62 in pyridine is treated with an excess of hydroxylamine hydrochloride and the reaction is stirred at room temperature for 2 d. The solution is concentrated in vacuo and the residue is chromatographed on silica gel to give the title compound.

EXAMPLE 64

Preparation of Ethyl 4-amino-5-oxo-1-phenyl-3-pyrrolidineacetate

A solution of the product of example 63 in EtOH is hydrogenated with 10% palladium on carbon at 60 psi at 60° C. Filtration and purification of the product on silica gel affords the title compound.

EXAMPLE 65

Preparation of cis-4-[(1H-Indol-2-ylcarbonyl)amino]-5-oxo-1-phenyl-3-pyrrolidineacetic acid The aminopyrrolidinone of Example 63 is coupled with indole-2-carboxylic acid according to the procedure described in Example 4 and the resulting ester is saponified to give the title homologated acid.

EXAMPLE 66

Preparation of 3-[[2-(Methoxymethyl)-1-pyrrolidinyl]imino]-1-phenyl-2-pyrrolidinone A solution of the product of Example 61 and chiral 1-amino-2-methoxymethylpyrrolidine (SAMP or RAMP; 1 equiv) in benzene is refluxed under Dean-Stark conditions for 20 h. After cooling, Et$_2$O is added and the mixture is washed with water. The organic layer is dried (MgO$_4$) and evaporated to give a residue which is chromatographed on silica gel to give the title compound.

EXAMPLE 67

Preparation of Ethyl 4-[[2-(methoxymethyl)-1-pyrrolidinyl]imino]-1-phenyl-5-oxo-3-pyrrolidineacetate To a solution of SAMP hydrazone of Example 66 or RAMP hydrazone of Example 66 in anhydrous THF at −78° C. is added dropwise a solution of tert-butyllithium (1.1 equiv) in n-hexane and the mixture is stirred for 2 h at −78° C. The solution of metalated hydrazone is cooled to −100° C. and a solution of ethyl bromoacetate (1.2 equiv) in anhydrous THF is added dropwise and the mixture is stirred for 1 h at −100° C. and then warmed slowly to room temperature over 15 h. Finally Et$_2$O is added and the mixture is washed with pH7-buffer and brine, dried (MgO$_4$) and evaporated under reduced pressure to give a residue which is chromatographed on silica gel eluting with EtOH/CH$_2$Cl$_2$ to give the title alkylated hydrazone in high diastereomeric excess.

EXAMPLE 68

Preparation of enantiomerically pure Ethyl cis-4-amino-5-oxo-1-phenyl-3-pyrrolidineacetate A solution of SAMP hydrazone of Example 67 or the RAMP hydrazone of Example 67 in EtOH is hydrogenated with 10% palladium on carbon at 1200 psi at 70° C. for 24 h. Filtration and evaporation of the filtrate gives a residue which is chromatographed on silica gel eluting with 2% EtOH/CH$_2$Cl$_2$ to give the desired title compound. Alternatively the hydrazone of Example 67 in anhydrous THF is treated with catecholborane followed by treatment with Raney Nickel. Filtration and evaporation of the filtrate gives a residue which is chromatographed on silica gel to give the title compound.

EXAMPLE 69

Preparation of enantiomerically pure cis-4-[(1H-Indol-2-ylcarbonyl)amino]-5-oxo-1-phenyl-3-pyrrolidineacetic acid To a solution of indole-2-carboxylic acid in DMF is added 1 equivalent of 1,1-carbonyldiimidazole. After stirring for 4 h at room temperature a solution of the aminopyrrolidinone of Example 68 in DMF is added. After stirring for 12 h at room temperature the reaction mixture is evaporated in vacuo to give a residue which is chromatographed on silica gel to give the desired amide. To a solution of the amide in 1:4 EtOH/THF is added a solution of lithium hydroxide (1.4 equiv) in H$_2$O and the resulting solution is stirred for 2 h at room temperature. The reaction mixture is then acidified to pH=2 with 1N HCl. Removal of the solvent gives a residue which is chromatographed on silica gel to give the title carboxylic acid as a single enantiomer.

EXAMPLE 70

Preparation of cis-N-(p-Methoxyphenyl)-3-carboxy-4-(1H-indol-2'-ylcarbonyl) aminoazetidin-2-one

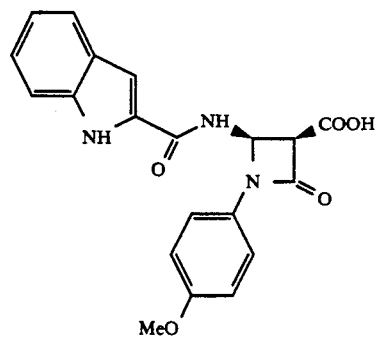

Cis-N-(p-methoxyphenyl)3-carboxy-4-dibenzylaminoazetidin-2-one t-butyl ester (T. Hiyama et al., J. Amer. Chem. Soc. (1989), 111, 6843) is hydrogenolyzed with 10% Pd-C/ammonium formate to afford cis-N-(p-methoxyphenyl)-3-carboxy-4-aminoazetidin-2-one t-butyl ester, which is not isolated but reacted directly with indole-2-carboxylic acid-carbonyldiimidazole/THF to give cis-N-(p-methoxyphenyl)-3-carboxy-4-(1H-indol-2'-yl)aminoazetidin-2-one t-butyl ester. Removal of the t-butyl ester with trifluoroacetic acid affords the title compound.

EXAMPLE 71

Preparation of trans-N-(p-Methoxyphenyl)-3-carboxy-4-(1H-indol-2'-yl carbonyl)aminozetidin-2-one

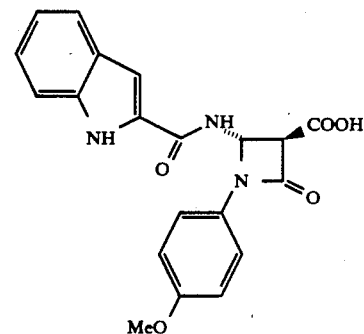

Following the procedure of Example 70, trans-N-(p-methoxyphenyl)-3-carboxy-4-dibenzylaminoazetidin-2-one t-butyl ester (T. Hiyama et al., J. Amer. Chem.

Soc. (1989), 111, 6843) is converted to the title compound.

EXAMPLE 72

Preparation of cis-N-(1'-Phenylethyl)-3-carboxy-4-(1H-indol-2"-ylcarbonyl)aminozetidin-2-one

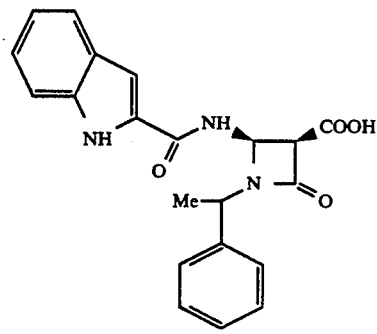

Following the procedure of Example 70, cis-N-(1'-phenylethyl)-3-carboxy-4-dibenzylaminoazetidin-2-one t-butyl ester (T. Hiyama et al., J. Amer. Chem. Soc. (1989), 111, 6843) is converted to the title compound.

EXAMPLE 73

Preparation of trans-N-(1'-Phenylethyl)-3-carboxy-4-(1H-indol-2"-ylcarbonyl)aminozetidin-2-one

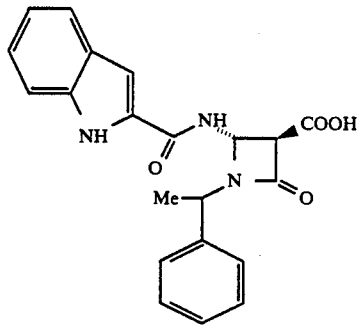

Following the procedure of Example 70, trans-N-(1'-phenylethyl)-3-carboxy-4-dibenzylaminoazetidin-2-one t-butyl ester (T. Hiyama et al., J. Amer. Chem. Soc. (1989), 111, 6843) is converted to the title compound.

EXAMPLE 74

Percent displacement of $^{125}$I-CCK-OP binding to rat pancreatic membrane and guinea pig brain homogenates by compounds of the instant invention at different concentrations was used to quantify CCK-A and CCK-B receptor binding, respectively.

Binding of 125-CCK-OP to rat pancreas (CCK-A) and guinea pig brain (CCK-B) homogenates.

Rat pancreas or guinea pig brain was homogenized in 50 and 20 volumes, respectively, of 50 mM Tris-HCl buffer (pH 7.8 at 25° C.) with a Brinkmann polytron homogenizer. The homogenates were centrifuged twice at 50,000 x g for 20 min with an intermediate rehomogenization in fresh buffer. The final pellets were resuspended in 20 volumes (brain) or 40 volumes (pancreas) of incubation buffer [50 mM Tris-HCl, 5 mM $MgCl_2$, 0.2% BSA, 5 mM dithiothreitol, 0.14 mg/ml bacitracin, pH 7.9 at 25° C.]. One milliliter of the final homogenate from brain or pancreas was diluted to 50 mL with incubation buffer to use in the binding assay.

Binding experiments were performed in a final volume of 1 mL in 13×100 mm borosilicate disposable culture tubes. To duplicate tubes were added 890 μL of freshly resuspended pancreas or brain homogenate; 73,000 dpm of $^1$I-CCK-OP (final concentration, 12 pM) and 10 μL of DMSO containing displacing agents (compounds or reference compounds, at the desired final concentrations). Nonspecific (nonsaturable) binding was determined in the presence of 1 μM unlabeled CCK-OP. After incubation for 30 min at 37° C. the binding was stopped by rapid filtration under a reduced pressure through glass fiber FPD-105 Whatman GF/B filters on Harvester and washed twice with 5 mL of ice-cold Tris buffer (50 mM Tris-HCl, pH 7.8). The radioactivity on the filters was counted in a gama counter. Radioactivity adsorbed to filters (filter blanks) was less than 0.5% of total radioactivity and was not displaced by the addition of unlabeled CCK-OP. Specific binding was defined as the excess binding over that in blanks containing 1 μM unlabeled CCK-OP.

Determination of $IC_{50}$ for displacing agents

The ability of compounds to displace $^{125}$I-CCK-OP binding to pancreatic or brain membrane homogenate was assessed in duplicate at concentrations varying from $10^{-5}$M to $10^{-7}$M. When the percent inhibition of specific $^{125}$I-CCK-OP binding by the displacing agent at the highest screening concentration was $\geq$50%, the compound was considered as active and $IC_{50}$ value was determined. The $IC_{50}$, the concentration of compound that inhibits 50% of specific $^{125}$I-CCK-OP binding, was estimated graphically.

Rat Gastric Emptying Protocol

A test meal for measuring gastric emptying in rats was prepared. Ten grams of methylcellulose (2% solution=15 centipoises; Aldrich Chemical Company, Milwaukee, Wisc. was added to 200ml of cold water and mixed at 20,000 rpm in a Waring blender to insure dispersion and hydration of the methylcellulose. In addition, two beef bouillon cubes (Wyler's, Columbus, Ohio) dissolved in 100 ml of warm water was added to the mixture, followed by 16 g of casein (Hammersten, Schwartz/Mann, Orangeburg, N.Y.), 8 g of powdered confectioners sugar and 8 g of cornstarch. The ingredients were mixed for two minutes at 20,000 rpm and the resultant test meal was refrigerated for 48 hours to allow trapped air to escape. Male Charles River Rats, Crl: COBS, CD (SD) BR Strain, 180-200 g body weight, were used in groups of six animals. The animals were food deprived for 24 hours prior to the experiment with access to water ad libitum. The compounds to be evaluated were prepared in a 0.5% aqueous methylcellulose solution. If insoluble, the mixture was homogenized for two minutes at 5500 rpm using a Try-R-Stir-R. The compounds were given intraperitoneally or intragastrically at a volume of 5 ml/kg, 60 minutes or 90 min, respectively, before the test meal. Control animals received only the vehicle. Cholecystokinin (100 μg/Kg, i.p.) was given 30 minutes before the test meal to delay gastric emptying by an effect elicited through CCK receptors. Sixty minutes after the test meal (2.0 ml/rat, i.g.), the rats were sacrificed by $CO_2$ asphyxiation. The stomachs were removed intact and weighed. The stomachs were kept opened, gently rinsed with tap water, blotted dry with paper toweling, and the empty stomach weighed. The difference between the weight of the full and empty stomach is indicative of the amount of meal remaining in the stomach. The amount of meal remaining in the stomach was subtracted from the weight of 3 ml of the test meal to determine the amount of food emptied from the stomach during the test. Weight of the test meal was determined by weighing three samples (3 ml) at the beginning and three samples at the end of each experiment and calculating the mean. The mean and standard error of the amount of meal emptied were calculated for at least 5 doses of compound, and expressed as percent change from control. Statistical testing was done for each dose of compound and an $ED_{50}$ value was estimated if significant ($p < 0.05$) activity was observed at any dose. The results of the above protocols for a representative number of compounds of the present invention are shown in Table B.

TABLE B

| Example # | COMPOUND | CCK-A BINDING RAT PANCREATIC MEMBRANES: IC50 (uM) | CCK-B BINDING GP BRAIN MEMBRANES: IC50 (uM) | CCK-DELAYED GASTRIC EMPTYING: $ED_{50}$ or % Reversal @ Dose |
|---|---|---|---|---|
| 41 | cis-4-[(2-naphthalenylcarbonyl)amino]-5-oxo-1-phenyl-3-pyrrolidinecarboxylic acid | 0.015 | 48% @ 10 | ED50 = 0.41 mpk IP |
| 41 | trans-4-[(2-naphthalenylcarbonyl)amino]-5-oxo-1-phenyl-3-pyrrolidinecarboxylic acid | 0.29 | 22% @ 10 | ED50 = 3.2 mpk IP |
| 44 | cis-1-(2-fluorophenyl)-4-[(2-naphthalenylcarbonyl]amoin]-5-oxo-3-pyrrolidinecarboxylic acid | 0.062 | 41% @ 10 | 86% @ 3 mpk IP ED50 = 1.7 mpk IP |
| 39 | trans-4-[(2-naphthalenylcarbonyl]amino-5-oxo-1-pentyl-3-pyrrolidinecarboxylic acid | >10 | | — |
| 28 | cis-1-(2-fluorophenyl)-5-oxo-4-[(3-quinolinylcarbonyl)amino]-5-oxo-3-pyrrolidinecarboxylic acid | 0.17 | >10 | |
| 27 | cis-5-oxo-1-pentyl-4-[(3-quinolinylcarbonyl)amino]-3-pyrrolidinecarboxylic acid, monohydrochloride | 0.25 | >10 | |
| 29 | cis-4-[(1-H-indol-2-ylcarbonyl)amino]-5-oxo-1-phenyl-3-pyrrolidinecarboxylic acid | 0.017 | 5.1 | 86.3% @ 1.0 mpk IP ED50 < 0.1 mpk IP |
| 30 | trans-4-[(1H-indol-2-ylcarbonyl)amino]-5-oxo-1-phenyl-3-pyrrolidinecarboxylic acid | 0.32 | | — |
| 35 (cis) | cis-4-[[(3,4-dichlorophenyl)carbonyl]amino]-5-oxo-1-phenyl-3-pyrrolidinecarboxylic acid | 0.058 | 35% @ 10 | 57.9% @ 3.0 mpk IP |
| 35 (trans) | trans-4-[[(3,4-dichlorophenyl)carbonyl]amino]-5-oxo-1-phenyl-3-pyrrolidinecarboxylic acid | >1.0 | >10 | |
| 32 | cis-4-[[(3,4-dichlorophenyl)carbonyl]amino]-5-oxo-1-phenyl-3-pyrrolidinecarboxylic acid | 0.3 | 49% @ 10 | |
| 46 (cis) | cis-4-[[(4-chlorophenyl)carbonyl]amino]-5-oxo-1-phenyl- | 1.6 | >10 | |

TABLE B-continued

| Example # | COMPOUND | CCK-A BINDING RAT PANCREATIC MEMBRANES: IC50 (uM) | CCK-B BINDING GP BRAIN MEMBRANES: IC50 (uM) | CCK-DELAYED GASTRIC EMPTYING: $ED_{50}$ or % Reversal @ Dose |
|---|---|---|---|---|
| | 3-pyrrolidinecarboxylic acid | | | |
| 46 (trans) | cis-4-[[(4-chlorophenyl)carbonyl]amino]-5-oxo-1-phenyl-3-pyrrolidinecarboxylic acid | 41 | >10 | |
| 45 | trans-4-[[(4-chlorophenyl)carbonyl]amino]-5-oxo-1-phenyl-3-pyrrolidinecarboxylic acid | >1.0 | >10 | |
| 40 | cis-4-[[(2-naphthalenylamino)carbonyl]amino]-5-oxo-1-pentyl-3-pyrrolidinecarboxylic acid | 2.8 | 10.0 | |
| 36 (cis) | cis-4-[[[(3,4-dichlorophenyl)amino]carbonyl]amino]-5-oxo-1-phenyl-3-pyrrolidinecarboxylic acid | 0.10 | 10.0 | |
| 36 (trans) | trans-4-[[[(3,4-dichlorophenyl)amino]carbonyl]amino-5-oxo-1-phenyl-3-pyrrolidinecarboxylic acid | >1.0 | 45% @ 10 | |
| 34 | cis-4-[[[(3,4-dichlorophenyl)amino]carbonyl]amino]-5-oxo-1-pentyl-3-pyrrolidinecarboxylic acid | 0.35 | 6.0 | |
| 47 | trans-4-[[[(4-chlorophenyl)amino]carbonyl]amino]-5-oxo-1-pentyl-3-pyrrolidinecarboxylic acid | >1.0 | — | |
| 47 | cis-4-[[[(4-chlorophenyl)amino]carbonyl]amino]-5-oxo-1-pentyl-3-pyrrolidinecarboxylic acid | >1.0 | | |
| 51 | trans-4-](3-indolyacetyl)amino]-5-oxo-1-phenyl-3-pyrrolidinecarboxylic acid | >1.0 | >10.0 | |
| | 1,1-dimethylethyl cis-4-[(2-naphthalenylcarbonyl)amino]-5-oxo-1-phenyl-3-pyrrolidinecarboxylate | 32% @ 1.0 | 35% @ 10 | |
| 53 | cis-1-[[3-[(2-naphthalenylcarbonyl)amino]-2-oxo-1-phenyl-4-pyrrolidinyl]carbonyl]pyrrolidine | 0.75 | 45% @ 10 | |
| 55 | trans-1-[[3-[(2-naphthalenylcarbonyl)amino]-2-oxo-1-phenyl-4-pyrrolidinyl]carbonyl]pyrrolidine | 27% @ 1.0 | 10.0 | |

What we claimed is:

1. A compound of the formula

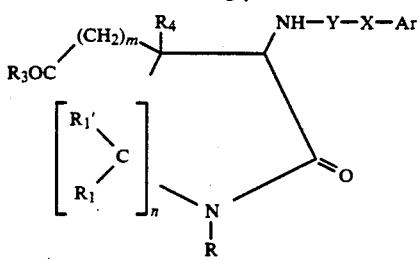

and isomers thereof; or a pharmaceutically acceptable acid or base addition salt thereof:
wherein
Ar is heterounsaturated ring having 5 or 6 carbon atoms wherein one or two of the carbon atoms is replaced by nitrogen, oxygen or sulfur; substituted heterounsaturated ring having 5 or 6 carbon atoms wherein one or two of the carbon atoms is replaced by nitrogen, oxygen or sulfur which can be substituted once or more by alkyl of 1 to 6 carbon atoms, halogen or trifluoromethyl; fused heterobicyclic hydrocarbon radical having 9 or 10 carbon atoms wherein one to three of the carbon atoms is replaced by nitrogen, oxygen or sulfur; substituted fused heterobicyclic hydrocarbon radical having 9 or 10 carbon atoms wherein one to three of the carbon atoms is replaced by nitrogen, oxygen or sulfur which can be substituted once or more by alkyl of 1 to 6 carbon atoms, halogen, trifluoromethyl, amino, alkyl or dialkyl substituted amino wherein the alkyl is 1 to 6 carbon atoms or alkoxy wherein the alkyl is 1 to 6 carbon atoms;

R is alkyl having 1 to 8 carbon atoms wherein one of the carbon atoms may be replaced by oxygen; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy; aralkyl wherein the alkyl is 1 to 8 carbon atoms; substituted aralkyl wherein the alkyl is 1 to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl or methylene dioxy;

X is a direct bond or a substituent selected from the group consisting of NH, oxygen or alkylene having 1 to 3 carbon atoms;

n is 1;

$R_1$ and $R_1'$ are each independently hydrogen or alkyl having 1 to 4 carbon atoms;

m is an integer from 0 to 3;

$R_3$ is OH, $OR_5$ wherein $R_5$ is alkyl having 1 to 6 carbon atoms, $NR_6R_7$ wherein $R_6$ and $R_7$ are each independently hydrogen or alkyl of 1 to 6 carbon atoms or $NR_8R_9$ which together form a five to seven membered ring wherein $R_8$ and $R_9$ together represent an alkylene group having four to six carbon atoms and one of the carbon atoms be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms;

$R_4$ is hydrogen or alkyl having 1 to 4 carbon atoms; and
Y is C=O or $SO_2$.

2. A compound according to claim 1 having the formula

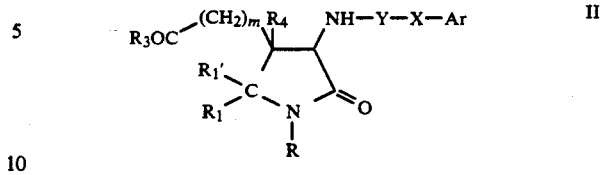

and isomers thereof; or a pharmaceutically acceptable acid or base addition salt thereof;
wherein
Ar is heterounsaturated ring having 5 or 6 carbon atoms wherein one or two of the carbon atoms is replaced by nitrogen, oxygen or sulfur; substituted heterounsaturated ring having 5 or 6 carbon atoms wherein one or two of the carbon atoms is replaced by nitrogen, oxygen or sulfur which can be substituted once or more by alkyl of 1 to 6 carbon atoms, halogen or trifluoromethyl;

R is alkyl having 1 to 8 carbon atoms wherein one of the carbon atoms may be replaced by oxygen; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy; aralkyl wherein the alkyl is 1 to 8 carbon atoms;

$R_1$ and $R_1'$ are each independently hydrogen or alkyl having 1 to 4 carbon atoms;

m is an integer from 0 to 3;

$R_3$ is OH or $OR_5$ wherein $R_5$ is alkyl having 1 to 6 carbon atoms;

$R_4$ is hydrogen;

Y is C=O or $SO_2$; and

X is a direct bond or a substituent selected from the group consisting of NH, oxygen or alkylene having 1 to 3 carbon atoms.

3. A compound according to claim 1 having the formula

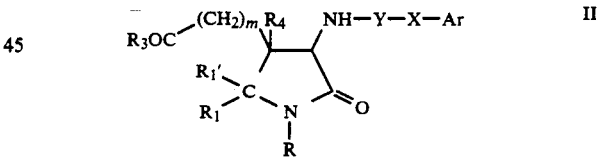

and isomers thereof; or a pharmaceutically acceptable acid or base addition salt thereof:
wherein
Ar is fused heterobicyclic hydrocarbon radical having 9 or 10 carbon atoms wherein one to three of the carbon atoms is replaced by nitrogen, oxygen or sulfur; substituted fused heterobicyclic hydrocarbon radical having 9 or 10 carbon atoms wherein one to three of the carbon atoms is replaced by nitrogen, oxygen or sulfur which can be substituted one or more by alkyl of 1 to 6 carbon atoms, halogen, trifluoromethyl, amino, alkyl or dialkyl amino wherein the alkyl is 1 to 6 carbon atoms, or alkoxy wherein the alkyl is 1 to 6 carbon atoms;

R is alkyl having 1 to 8 carbon atoms; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl or methylene dioxy; aralkyl wherein the alkyl is 1 to 8 carbon atoms; substituted aralkyl wherein the alkyl is 1 to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl or methylene dioxy;

$R_1$ and $R_1'$ are each independently hydrogen or alkyl having 1 to 4 carbon atoms;

m is an integer from 0 to 3;

$R_3$ is OH, $OR_5$ wherein $R_5$ is alkyl having 1 to 6 carbon atoms, $NR_6R_7$ wherein $R_6$ and $R_7$ are each independently hydrogen or alkyl of 1 to 6 carbon atoms or $NR_8R_9$ which together form a five to seven membered ring wherein $R_8$ and $R_9$ together represent an alkylene group having four to six carbon atoms and one of the carbon atoms may be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms;

$R_4$ is hydrogen;

Y is C=O; and

X is a direct bond or a substituent selected from the group consisting of NH, oxygen or alkylene having 1 to 3 carbon atoms.

4. A compound according to claim 3 which is cis-4-[(1H-indol-2-ylcarbonyl)amino]-5-oxo-1-phenyl-3-pyrrolidinecarboxylic acid.

5. A compound according to claim 3 which is cis-1-(2-fluorophenyl)-5-oxo-4-[(3-quinolinylcarbonyl)amino]-5-oxo-3-pyrrolidinecarboxylic acid.

6. A compound according to claim 3 which is trans-4-[(1H-indol-3-ylacetyl)amino]-5-oxo-1-phenyl-3-pyrrolidinecarboxylic acid.

7. A compound according to claim 3 which is cis-5-oxo-1-pentyl-4-[(3-quinolinylcarbonyl)amino]-3-pyrrolidinecarboxylic acid, monohydrochloride.

8. A compound according to claim 3 which is trans-4-[(1H-indol-2-ylcarbonyl)amino]-5-oxo-1-phenyl-3-pyrrolidinecarboxylic acid.

9. A compound according to claim 3 which is trans-1-phenyl-4-(1-pyrrolidinylcarbonyl)-3-pyrrolidinyl]-1H-indole-2-carboxamide.

10. A compound according to claim 3 which is cis-4-[(1H-indol-2-ylcarbonyl)amino]-5-oxo-1-(phenylmethyl)-3-pyrrolidinecarboxylic acid.

11. A compound according to claim 3 which is cis-4-[(1H-indazol-3-ylcarbonyl)amino]-5-oxo-1-phenyl-3-pyrrolidinecarboxylic acid.

12. A compound according to claim 1 which is cis-5-oxo-1-phenyl-4-[(2-pyrazinylcarbonyl)amino]-3-pyrrolidinecarboxylic acid.

13. A pharmaceutical composition useful for treating and preventing cholecystokinin related disorders of the gastrointestinal, central nervous and appetite regulatory systems of mammals comprising at least one compound according to claim 1, together with one or more nontoxic pharmaceutically acceptable carriers.

14. A method for treating and preventing cholecystokinin related disorders of the gastrointestinal, central nervous, and appetite regulatory systems of mammals comprising administering a therapeutically effective dose of at least one compound of claim 1 to a mammal in need of such treatment.

15. A pharmaceutical composition according to claim 13 wherein said compound is selected from the group consisting of
cis-4-[(1H-indol-2-ylcarbonyl)amino]-5-oxo-1-phenyl-3-pyrrolidinecarboxylic acid;
cis-1-(2-fluorophenyl)-5-oxo-4-[(3-quinolinylcarbonyl)amino]-5-oxo-3-pyrrolidinecarboxylic acid;
trans-4-[(1H-indol-3-ylacetyl)amino]-5-oxo-1-phenyl-3-pyrrolidinecarboxylic acid;
cis-5-oxo-1-pentyl-4-[(3-quinolinylcarbonyl)amino]-3-pyrrolidinecarboxylic acid, monohydrochloride;
trans-4-[(1H-indol-2-ylcarbonyl)]-5-oxo-1-phenyl-3-pyrrolidinecarboxylic acid;
trans-N-[2-oxo-1-phenyl-4-(1-pyrrolidinylcarbonyl)-3-pyrrolidinyl]-1H-indole-2-carboxamide;
cis-4-[(1H-indol-2-ylcarbonyl)amino]-5-oxo-1-(phenylmethyl)-3-pyrrolidinecarboxylic acid;
cis-4-[(1H-indazol-3-ylcarbonyl)amino]-5-oxo-1-phenyl-3-pyrrolidinecarboxylic acid;
and
cis-5-oxo-1-phenyl-4-[(2-pyrazinylcarbonyl)amino]-3-pyrrolidinecarboxylic acid.

16. A method according to claim 14 wherein said compound is selected from the group consisting of
cis-4-[(1H-indol-2-ylcarbonyl)amino]-5-oxo-1-phenyl-3-pyrrolidinecarboxylic acid;
cis-1-(2-fluorophenyl)-5-oxo-4-[(3-quinolinylcarbonyl)amino]-5-oxo-3-pyrrolidinecarboxylic acid;
trans-4-[(1H-indol-3-ylacetyl)amino]-5-oxo-1-phenyl-3-pyrrolidinecarboxylic acid;
cis-5-oxo-1-pentyl-4-[(3-quinolinylcarbonyl)amino]-3-pyrrolidinecarboxylic acid, monohydrochloride;
trans-4-[(1H-indol-2-ylcarbonyl)]amino]-5-oxo-1-phenyl-3-pyrrolidinecarboxylic acid;
trans-N-[2-oxo-1-phenyl-4-(1-pyrrolidinylcarbonyl)-3-pyrrolidinyl]-1H-indole-2-carboxamide;
cis-4-[(1H-indol-2-ylcarbonyl)amino]-5-oxo-1-(phenylmethyl)-3-pyrrolidinecarboxylic acid;
cis-4-[(1H-indazol-3-ylcarbonyl)amino]-5-oxo-1-phenyl-3-pyrrolidinecarboxylic acid;
and
cis-5-oxo-1-phenyl-4-[(2-pyrazinylcarbonyl)amino]-3-pyrrolidinecarboxylic acid.

17. A compound of the formula

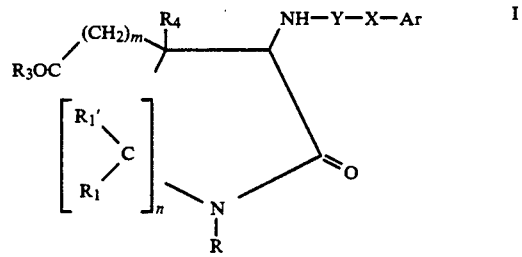

and isomers thereof; or a pharmaceutically acceptable acid or base addition salt thereof:
wherein
Ar is aryl; substituted aryl which can be substituted one or more by alkyl of 1 to 6 carbon atoms, alkoxy wherein the alkyl is 1 to 6 carbon atoms, trifluoromethyl, halogen, amino, alkyl or dialkyl substituted amino wherein the alkyl is 1 to 6 carbon atoms, fused bicyclic aromatic hydrocarbon radical having 9 or 10 carbon atoms; substituted fused bicyclic aromatic hydrocarbon radical having 9 or 10 carbon atoms which can be substituted one or more by alkyl of 1 to 6 carbon atoms, halogen, trifluoromethyl, amino, alkyl or dialkyl substituted amino wherein the alkyl is 1 to 6 carbon atoms, or alkoxy wherein the alkyl is 1 to 6 carbon atoms;

R is alkyl having 1 to 8 carbon atoms wherein one of the carbon atoms may be replaced by oxygen; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy; aralkyl wherein the alkyl is 1 to 8 carbon atoms; substituted aralkyl wherein the alkyl is 1 to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy;

X is a direct bond or a substituent selected from the group consisting of NH, oxygen or alkylene having 1 to 3 carbon atoms;

n is 1;

$R_1$ and $R_1'$ are each independently hydrogen or alkyl having 1 to 4 carbon atoms;

m is an integer from 0 to 3;

$R_3$ is $NR_8R_9$ which together form a five to seven membered ring wherein $R_8$ and $R_9$ together represent an alkylene group having four to six carbon atoms and one of the carbon atoms may be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms;

$R_4$ is hydrogen or alkyl having 1 to 4 carbon atoms;

Y is C=O or $SO_2$.

18. A compound according to claim 17 having the formula

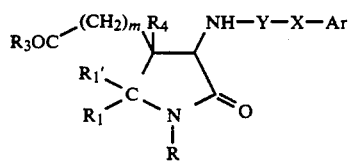

and isomers thereof; or a pharmaceutically acceptable acid or base addition salt thereof:

wherein

Ar is aryl; fused bicyclic aromatic hydrocarbon radical having 9 or 10 carbon atoms; substituted fused bicyclic aromatic hydrocarbon radical having 9 or 10 carbon atoms which can be substituted one or more by alkyl of 1 to 6 carbon atoms, halogen, trifluoromethyl, amino, alkyl or dialkyl substituted amino wherein the alkyl is 1 to 6 carbon atoms, or alkoxy wherein the alkyl is 1 to 6 carbon atoms;

R is alkyl having 1 to 8 carbon atoms wherein one of the carbon atoms may be replaced by oxygen; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl or methylene dioxy; aralkyl wherein the alkyl is 1 to 8 carbon atoms; substituted aralkyl wherein the alkyl is 1 to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy;

$R_1$ and $R_1'$ are each independently hydrogen or alkyl having 1 to 4 carbon atoms;

m is an integer from 0 to 3;

$R_3$ is $NR_8R_9$ which together form a five to seven membered ring wherein $R_8$ and $R_9$ together represent an alkylene group having four to six carbon atoms and one of the carbon atoms may be optionally replaced by oxygen, nitrogen or $NR_{10}$ wherein $R_{10}$ represents hydrogen, or alkyl having 1 to 6 carbon atoms or aralkyl wherein the alkyl is 1 to 6 carbon atoms;

$R_4$ is hydrogen;

Y is C=O or $SO_2$; and

X is a direct bond or a substituent selected from the group consisting of NH, oxygen or alkylene having 1 to 3 carbon atoms.

19. A compound according to claim 18 which is cis-1-[[3-[(2-naphthalenylcarbonyl)amino]-2-oxo-1-phenyl-4-pyrrolidinyl]carbonyl]pyrrolidine.

20. A compound according to claim 18 which is trans-1-[[3-[(2-naphthalenylcarbonyl)amino]-2-oxo-1-phenyl-4-pyrrolidinyl]carbonyl]pyrrolidine.

21. A pharmaceutical composition useful for treating and preventing cholecystokinin related disorders of the gastrointestinal, central nervous and appetite regulatory systems of mammals comprising at least one compound according to claim 17, together with one or more non-toxic pharmaceutically acceptable carriers.

22. A pharmaceutical composition according to claim 21 wherein said compound is selected from the group consisting of cis-1-[[3-[(2-naphthalenylcarbonyl)amino]-2-oxo-1-phenyl-4-pyrrolidinyl]carbonyl]pyrrolidine and trans-1-[[3-[(2-naphthalenylcarbonyl)amino]-2-oxo-1-phenyl-4-pyrrolidinyl]carbonyl]pyrrolidine.

23. A method for treating and preventing cholecystokinin related disorders of the gastrointestinal, central nervous, and appetite regulatory systems of mammals comprising administering a therapeutically effective dose of at least one compound of claim 17 to a mammal in need of such treatment.

24. A compound of the formula

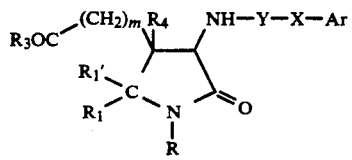

and isomers thereof; or a pharmaceutically acceptable acid or base addition salt thereof:

wherein

Ar is aryl; substituted aryl which can be substituted one or more by alkyl of 1 to 6 carbon atoms, alkoxy wherein the alkyl is 1 to 6 carbon atoms, trifluoromethyl, halogen, amino, alkyl or dialkyl substituted amino wherein the alkyl is 1 to 6 carbon atoms, fused bicyclic aromatic hydrocarbon radical having 9 or 10 carbon atoms; substituted fused bicyclic aromatic hydrocarbon radical having 9 or 10 carbon atoms which can be substituted one or more by alkyl of 1 to 6 carbon atoms, halogen, trifluoromethyl, amino, alkyl or dialkyl substituted amino wherein the alkyl is 1 to 6 carbon atoms, or alkoxy wherein the alkyl is 1 to 6 carbon atoms;

R is alkyl having 1 to 8 carbon atoms wherein one of the carbon atoms may be replaced by oxygen; aryl; substituted aryl which can be substituted one or more by halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy; aralkyl wherein the alkyl is 1 to 8 carbon atoms; substituted aralkyl wherein the alkyl is 1 to 8 carbon atoms and the substituent or substituents are selected from the group consisting of halogen, alkyl having 1 to 6 carbon atoms, alkoxy wherein the alkyl is 1 to 6 carbon atoms, amino, alkyl or dialkyl substituted amino wherein the alkyl is 1 to 6 carbon atoms, trifluoromethyl, or methylene dioxy;

X is a direct bond or a substituent selected from the group consisting of NH, oxygen or alkylene having 1 to 3 carbon atoms.

25. A compound according to claim 24 which is cis-4-[[(3,4-dichlorophenyl)sulfonyl]amino]-5-oxo-1-phenyl-3-pyrrolidinecarboxylic acid.

26. A compound according to claim 24 which is cis-4-[(2-naphthalenylsulfonyl)amino]-5-oxo-1-phenyl-3-pyrrolidinecarboxylic acid.

27. A pharmaceutical composition useful for treating and preventing cholecystokinin related disorders of the gastrointestinal, central nervous and appetite regulatory systems of mammals comprising at least one compound according to claim 24, together with one or more nontoxic pharmaceutically acceptable carriers.

28. A pharmaceutical composition according to claim 27 wherein said compound is selected from the group consisting of
cis-4-[(2-naphthalenylsulfonyl)amino]-5-oxo-1-phenyl-3-pyrrolidinecarboxylic acid
and
cis-4-[[(3,4-dichlorophenyl)sulfonyl]amino]-5-oxo-1-phenyl-3-pyrrolidinecarboxylic acid.

29. A method for treating and preventing cholecystokinin related disorders of the gastrointestinal, central nervous, and appetite regulatory systems of mammals comprising administering a therapeutically effective dose of at least one compound of claim 24 to a mammal in need of such treatment.

* * * * *

UNITED STATES PATENT AND TRADEMARK OFFICE
CERTIFICATE OF CORRECTION

PATENT NO. : 5,314,886
DATED : May 24, 1994
INVENTOR(S) : Becker, et al.

It is certified that error appears in the above-indentified patent and that said Letters Patent is hereby corrected as shown below:

Column 1, line 48, reading "Central" should read -- central --.

Column 2, line 6, reading "invention." should read -- invention; --.

Column 6, line 6, reading "9 to 10" should read -- 9 or 10 --.

Column 6, line 19, reading "; to 8" should read -- 1 to 8 --.

Column 7, line 13, reading "or bas" should read -- or base --.

Column 9, line 55, the formula reading

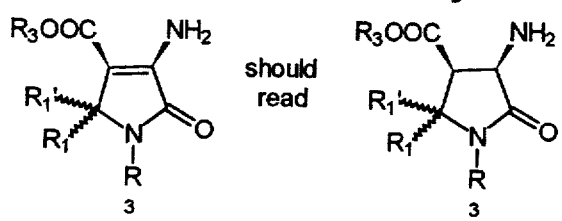

Column 13, line 24, reading "of (Scheme III)" should read -- of Formula I (Scheme III) --.

Column 21, line 30, reading "HO" should read -- $H_2O$ --.

Column 21, line 62, reading "which as" should read -- which was --.

Column 22, line 15, reading "I.32" should read -- 1.32 --.

Column 24, line 44, reading "$CH_2Cl$" should read -- $CH_2Cl_2$ --.

UNITED STATES PATENT AND TRADEMARK OFFICE
CERTIFICATE OF CORRECTION

PATENT NO. : 5,314,886  Page 2 of 4
DATED : May 24, 1994
INVENTOR(S) : Becker, et al.

It is certified that error appears in the above-indentified patent and that said Letters Patent is hereby corrected as shown below:

Column 25, line 48, reading "EtOH/CH$_2$Cl$_2$ ∫" should read -- EtOH/CH$_2$Cl$_2$ --.

Column 28, line 34, reading "C$_{23}$H$_{33}$N$_3$O$_4$" should read -- C$_{25}$H$_{33}$N$_3$O$_4$ --.

Column 32, line 29, reading "MS calcd" should read -- MS calcd for --.

Column 34, line 26, reading "was suspended" should read -- was resuspended --.

Column 34, line 48, reading "H$_2$C" should read -- H$_2$O --.

Column 39, line 61, reading "EtOH/" should read -- MeOH/ --.

Column 40, line 65, reading "Found" should read -- Found: --.

Column 41, line 5, the formula reading

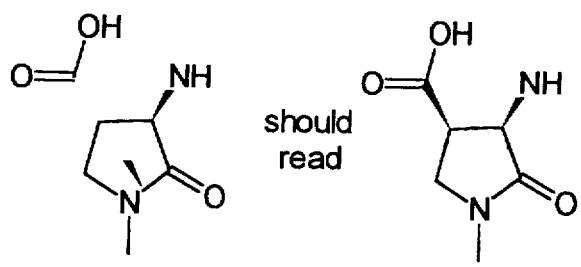

Column 41, line 20, reading "cis-1-" should read -- cis-4- --.

Column 43, line 59, reading "ester of" should read -- ester --.

UNITED STATES PATENT AND TRADEMARK OFFICE
CERTIFICATE OF CORRECTION

PATENT NO. : 5,314,886          Page 3 of 4
DATED      : May 24, 1994
INVENTOR(S): Becker , et al.

It is certified that error appears in the above-indentified patent and that said Letters Patent is hereby corrected as shown below:

Column 43, line 67, reading "316," should read -- 326, --.

Column 44, line 65, reading "$CH_2Cl_2$" should read -- $CHCl_3$ --.

Column 44, line 68, reading "$CH_2Cl_2$" should read -- $CHCl_3$ --.

Column 45, line 60, reading "example 20" should read -- example 30 --.

Column 45, line 67, reading "$C_{24}H_{24}N_4O_4$" should read -- $C_{24}H_{24}N_4O_3$ --.

Column 52, line 9, reading "$^1$I-CCK-OP" should read -- $^{125}$I-CCK-OP --.

Column 52, line 33, reading "and $IC_{50}$" --and an $IC_{50}$ --.

Column 53, line 31, reading "amoin]" should read -- amino] --.

Column 55, line 18, reading "10.0" should read -- 3.9 --.

Column 55, line 47, reading "trans-4-]" should read -- trans-4-[ --.

Column 57, line 63, reading "atoms be" should read -- atoms may be --.

Column 61, line 50, reading "Ar is aryl;" should read -- Ar is --.

UNITED STATES PATENT AND TRADEMARK OFFICE
CERTIFICATE OF CORRECTION

PATENT NO. : 5,314,886
DATED : May 24, 1994
INVENTOR(S) : Becker, et al.

It is certified that error appears in the above-indentified patent and that said Letters Patent is hereby corrected as shown below:

Column 59, line 45, reading "trans-1-" should read -- trans-N-[2-oxo-1- --.

Column 63, line 21, change "atoms." to --atoms;--; and between lines 21 and 22, insert the following:

--$R_1$ and $R_1'$ are each independently hydrogen or alkyl having 1 to 4 carbon atoms; m is an integer from 0 to 3; $R_3$ is OH, $OR_5$ wherein $R_5$ is alkyl having 1 to 6 carbon atoms or $NR_6R_7$ wherein $R_6$ and $R_7$ are each independently hydrogen or alkyl of 1 ato 6 carbon atoms; $R_4$ is hydrogen or alkyl having 1 to 4 carbon atoms; Y is $SO_2$.--.

Signed and Sealed this

Fifteenth Day of July, 1997

Attest:

BRUCE LEHMAN

*Attesting Officer*      Commissioner of Patents and Trademarks